US008377700B2

(12) United States Patent
Strano et al.

(10) Patent No.: US 8,377,700 B2
(45) Date of Patent: Feb. 19, 2013

(54) SYSTEMS AND METHODS USING PHOTOLUMINESCENT NANOSTRUCTURE BASED HYDROGELS

(75) Inventors: Michael S. Strano, Lexington, MA (US); Paul W. Barone, Jamaica Plain, MA (US); Jin-Ho Ahn, Gyeonggi-Do (KR); Ardemis Anoush Boghossian, White Lake, MI (US); Rene Ortiz-Garcia, Dresden (DE); Hyeonseok Yoon, Gwangju (KR); Jingqing Zhang, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 12/659,193

(22) Filed: Feb. 26, 2010

(65) Prior Publication Data
US 2010/0279421 A1 Nov. 4, 2010

Related U.S. Application Data

(60) Provisional application No. 61/155,882, filed on Feb. 26, 2009.

(51) Int. Cl.
*G01N 21/76* (2006.01)
*G01N 21/00* (2006.01)

(52) U.S. Cl. ............ 436/86; 436/163; 436/172; 435/29; 435/4; 435/7.9; 435/7.1; 435/287.2; 435/283.1

(58) Field of Classification Search .................... 436/86, 436/163, 172; 435/29, 4, 7.9, 7.1, 287.2, 435/283.1, 9
See application file for complete search history.

(56) References Cited

U.S. PATENT DOCUMENTS

| 6,362,011 | B1 * | 3/2002 | Massey et al. | 436/526 |
|---|---|---|---|---|
| 6,821,730 | B2 * | 11/2004 | Hannah | 435/6.11 |
| 6,878,361 | B2 * | 4/2005 | Clarke et al. | 423/461 |
| 2004/0224380 | A1 * | 11/2004 | Chou et al. | 435/29 |
| 2007/0292896 | A1 * | 12/2007 | Strano et al. | 435/7.9 |

OTHER PUBLICATIONS

Barone, Paul W., et al. "In vivo fluorescence detection of glucose using a single-walled carbon nanotube optical senson: design, fluorophore properties, advantages, and disadvantages." Analytical Chemistry, Dec. 1, 2005, vol. 77, No. 23, p. 7556-7562.
Luqi, Liu, et al. " Mechanical properties of functionalized single-walled carbon-nanotube/poly(vinyl acohol) nanocomposites" Advanced Functional Materials Wiley-VCH Germany, vol. 15, No. 6, p. 975-980, Jun. 2005.
Xin Tong, et al. "Swelling and mechanical behaviors of carbon nanotube/poly(vinyl alcohol) hybrid hydrogels" Materials Letters Elsevier Netherlands, Apr. 2007, vol. 61, No. 8-9, p. 1704-1706.
Bhattacharyya, Sanjib, et al. "Carbon nanotubes as structural nanofibers for hyaluric acid hydrogel scaffolds" Biomarcomolecules, Feb. 2008, vol. 9, No. 2, p. 505-509.

(Continued)

*Primary Examiner* — Christine T Mui
(74) *Attorney, Agent, or Firm* — Steptoe & Johnson LLP

(57) ABSTRACT

Systems and methods related to compositions including hydrogels and photoluminescent nanostructures are described. The compositions can undergo a change in a physical, chemical, dielectric, or other property upon exposure to an altering stimulus. Changes in one or more properties of the hydrogel may impart a change in the photoluminescence of the nanostructures embedded in the hydrogel.

28 Claims, 39 Drawing Sheets

OTHER PUBLICATIONS

Sung, J. et al. "Sequential delivery of dexamethasone and VEGF to control local tissue response for carbon nanotube fluorescence based micro-capillary implantable sensors" Biomaterials, Elsevier Science Publishers, vol. 30, No. 4, p. 622-631, Feb. 1, 2009.

Doretti, Lucio, et al. "PEG-modified glucose oxidase immobilized on a PVA cryogel membrane for amperometric biosensor applications" Talanta, vol. 45, No. 5, p. 891-898, Mar. 1998.

Wong, Fui-Ling, et al. "Comparative study of poly(vinyl alcohol)-based support materials for the immobilization of glucose oxidase" Journal of Chemical Technology and Biotechnology, vol. 83, No. 1, p. 41-46, Jan. 2008.

Zhang, Yongjun, et al. "Synthesis and volume phase transitions of glucose-sensitive microgels" Biomacromolecules, Nov. 2006, vol. 7, No. 11, p. 3196-3201.

Barone, Paul W., et al. "Modulation of single-walled carbon nanotube photoluminescence by hydrogel swelling" ACS Nano, Dec. 22, 2009, vol. 3, No. 12, p. 3869-3877.

Barone, Paul W., et al. "Single walled carbon nanotubes as reporters for the optical detection of glucose" Journal of Diabetes Science and Technology, 2009, vol. 3, No. 2, p. 242-252.

Koutsopoulos Sotirios, et al. "Controlled release of functional proteins through designer self-assembling peptide nanofiber hydrogel scaffold" Proceedings of the National Academy of Sciences in the United States of America, Mar. 2009, vol. 106, No. 12, p. 4623-4628.

International Search Report for PCT/US2010/025593 filed Feb. 26, 2010.

International Preliminary Report on Patentability and Written Opinion of the International Searching Authority dated Sep. 9, 2011 for PCT/US2010/025593.

\* cited by examiner

SYSTEMS AND METHODS USING PHOTOLUMINESCENT NANOSTRUCTURE BASED HYDROGELS

CLAIM OF PRIORITY

This application claims priority to provisional U.S. Patent Application 61/155,882, filed Feb. 26, 2009, which is incorporated by reference in its entirety.

FEDERALLY SPONSORED RESEARCH OR DEVELOPMENT

This invention was made with government support under Grant No. NSF0753020 awarded by the National Science Foundation. The government has certain rights in this invention.

TECHNICAL FIELD

The present invention generally relates to compositions including hydrogels containing photoluminescent nanostructures, wherein the compositions are responsive to an external stimulus, and related methods.

BACKGROUND

Sensors for controlling and processing light for in-vivo applications are of particular interest in the biomedical field. For example, in-vivo sensors could be used to detect glucose levels in diabetes patients. Several photonics applications have been proposed for in-vivo sensing such as, for example, surface enhanced Raman spectroscopy (SERS). However, many proposed methods are expensive, require high resolution, and involve the use of bulky equipment.

Accordingly, improved methods are needed.

SUMMARY

Systems and methods using compositions including stimuli-responsive hydrogels containing photoluminescent nanostructures are described. The subject matter involves, in some cases, interrelated products, alternative solutions to a particular problem, and/or a plurality of different uses of one or more systems and/or articles.

In one aspect, methods are described. In one set of embodiments, the method includes providing a composition comprising a stimulus-responsive hydrogel, and a photoluminescent nanostructure embedded in the hydrogel. The method may further include exposing the composition to a stimulus, thereby causing a change in a property of the composition. In addition, the method may include determining the change in the property of the composition, thereby determining the stimulus.

In one set of embodiments, the method includes a method for the determination of an analyte. The method may include exposing a composition including a stimulus-responsive hydrogel and a photoluminescent nanostructure embedded in the hydrogel to a sample suspected of containing an analyte. The analyte may, if present, interact with the composition to alter a structure of the composition, causing a change in the photoluminescence emission of the photoluminescent nanostructure. In addition, the method may include determining the change in photoluminescence emission of the photoluminescent nanostructure, thereby determining the analyte.

In another aspect, compositions are described. The composition may include a stimulus-responsive hydrogel, and a photoluminescent nanostructure embedded in the hydrogel.

Other aspects, embodiments and features will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All documents, including patent applications and patents, incorporated herein by reference are incorporated by reference in their entirety. In case of conflict, the present specification, including definitions, will control.

BRIEF DESCRIPTION OF THE DRAWINGS

Non-limiting embodiments will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand what is depicted. In the figures:

FIGS. 31 and 32 illustrate the platform and fluorescence data obtained from the platform.

FIG. 36 includes plot of fluorescence following addition of glucose.

FIG. 37 includes calibration curves.

DETAILED DESCRIPTION

Figure 1:
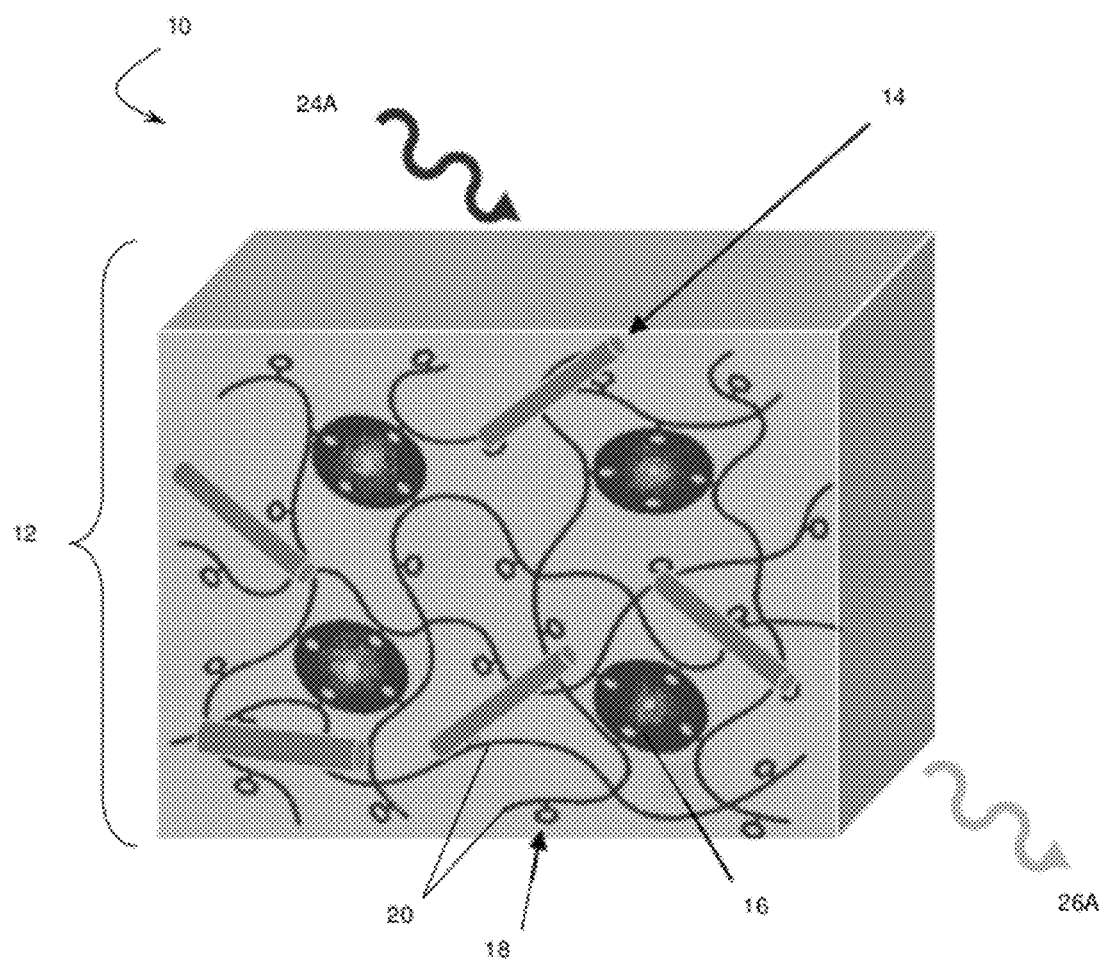
FIGS. 1-2 include schematic diagrams of a composition, according to one set of embodiments.

Systems and methods related to compositions including hydrogels and photoluminescent nanostructures are described. The compositions can undergo a change in a physical, chemical, dielectric, or other property upon exposure to an altering stimulus. Changes in one or more properties of the hydrogel may impart a change in the photoluminescence of the nanostructures embedded in the hydrogel. Not wishing to be bound by any theory, prior to exposure to the stimulus, one or more parts of the hydrogel may be forced to be in closer proximity to the photoluminescent nanostructures than would otherwise be observed in the presence of the stimulus, or some other kinetic, thermodynamic, or other interaction between the hydrogel and the photoluminescent nanostructures is different in the absence or in the presence of the stimulus. In this configuration, the composition may exist in a different energy state (for example, a relatively higher energy state) compared to the energy state it would assume upon exposure to the stimulus. Once exposed to the stimulus, the parts of the hydrogel that were forced to be in close proximity to the photoluminescent nanostructures may be allowed to change to a different energy state, for example to relax to a relatively lower energy state. The relaxation may cause a change in a property of the composition (e.g., local dielectric constant around the photoluminescent nanostructures), leading to a change in the photoluminescent behavior of the nanostructures. The change in the photoluminescence can include a change in photoluminescence intensity, a change in peak wavelength, a Raman shift, or a combination thereof.

Compositions of the invention may be useful in a wide variety of applications, such as the detection of glucose, beta-estradiol, small proteins (e.g., insulin), antigens (e.g., prostate specific antigen), changes in temperature, or changes in pH, among others.

Some embodiments can be particularly advantageous due to the biocompatible nature of hydrogels. Hydrogels are particularly resistant to biological fouling. When sensors are used in vitro, biological entities (e.g., endothelial cells, proteins, etc.) may adhere to the sensor and block and/or consume the compound to be detected (e.g., glucose). When this occurs, the sensor may fail to detect the presence of the compound, or may detect a concentration of the compound that is lower than the amount in the surrounding fluid (e.g., blood), thus rendering the sensor inaccurate or unusable. Because hydrogels can be resistant to biological fouling, such disadvantages can be mitigated. In addition, in some embodiments where the hydrogels are not biodegradable, undesired leaching of nanostructures may be prevented.

As used herein, the term "hydrogel" is given its ordinary meaning in the art and refers to a material comprising a polymer network that is able to trap and contain water. The hydrogel may include polymer chains that are crosslinked, either directly or via a crosslinking agent. The degree of crosslinking may be varied, in some cases, to tailor the extent to which the gel absorbs or retains fluids. Examples of polymers capable of forming hydrogels include, collagen, silicon-containing polymers, polyacrylamides, crosslinked polymers (e.g., polyethylene oxide, polyAMPS and polyvinylpyrrolidone), polyvinyl alcohol, acrylate polymers (e.g., sodium polyacrylate), and copolymers with an abundance of hydrophilic groups. The hydrogels described herein may be responsive to one or more external stimuli (i.e., a "stimulus-responsive hydrogel"), as described more fully below.

As used herein, the term "nanostructure" refers to articles having at least one cross-sectional dimension of less than about 1 μm, less than about 500 nm, less than about 250 nm, less than about 100 nm, less than about 75 nm, less than about 50 nm, less than about 25 nm, less than about 10 nm, or, in some cases, less than about 1 nm. Examples of nanostructures include nanotubes (e.g., carbon nanotubes), nanowires (e.g., carbon nanowires), graphene, and quantum dots, among others. In some embodiments, the nanostructures include a fused network of atomic rings.

A "photoluminescent nanostructure," as used herein, refers to a class of nanostructures that are capable of exhibiting photoluminescence. Examples of photoluminescent nanostructures include, but are not limited to, single-walled carbon nanotubes ("SWNT"), double-walled carbon nanotubes, semi-conductor quantum dots, semi-conductor nanowires, and graphene, among others. In some embodiments, photoluminescent nanostructures exhibit fluorescence. In some instances, photoluminescent nanostructures exhibit phosphorescence.

In one set of embodiments, compositions including a stimulus-responsive hydrogel and a photoluminescent nanostructure embedded in the hydrogel are provided. When exposed to an external stimulus, at least one physical, chemical, or dielectric characteristic of the composition may be modified. In some embodiments, exposure to an external stimulus involves the stimulus interacting directly with a component of the composition, causing the characteristics of the composition to be modified. In other embodiments, exposure to an external stimulus involves the stimulus interacting indirectly with a component of the composition, modifying the characteristics of the composition. In some cases, the change may be a dimensional change (e.g., volumetric change). For example, the dimensional change may include swelling or de-swelling of the hydrogel. In some embodiments, the change may include a change in the extent of cross-linking (e.g., physical and/or chemical cross-linking) in the hydrogel. In some instances, the swelling and/or de-swelling of the hydrogel may be dependent upon the amount of cross-linking within the hydrogel. In some embodiments, the change may include a change in the electronic properties. For example, the change in electronic properties of the composition may involve electron transfers at the nanotube. In some embodiments, the change may include a chemical change. The chemical change can be the result of enzymatic activity. In some instances, the change in electronic properties may be dependent upon the chemical change resulting from enzymatic activity.

In some embodiments, the change in the characteristic of the composition may affect the electromagnetic radiation emitted by the photoluminescent nanostructure. Changes in the electromagnetic radiation emitted may include increasing intensity, decreasing intensity, quenching, unquenching, bleaching, unbleaching, increasing the wavelength of the emission, and/or decreasing the wavelength of the emission, where the changes may be reversible or irreversible. Intensity refers to the photoluminescent intensity and can include fluorescence intensity, phosphorescence intensity, real-time intensity, normalized intensity, or initial intensity. Not wishing to be bound by any theory, a change in swelling and/or cross-linking and/or chemical properties and/or electronic properties within the hydrogel may change the local dielectric constant around the photoluminescent nanostructure. The change in the local dielectric constant may, in turn, lead to a change in the wavelength of electromagnetic radiation emitted by the photoluminescent nanostructure.

Figure 2:
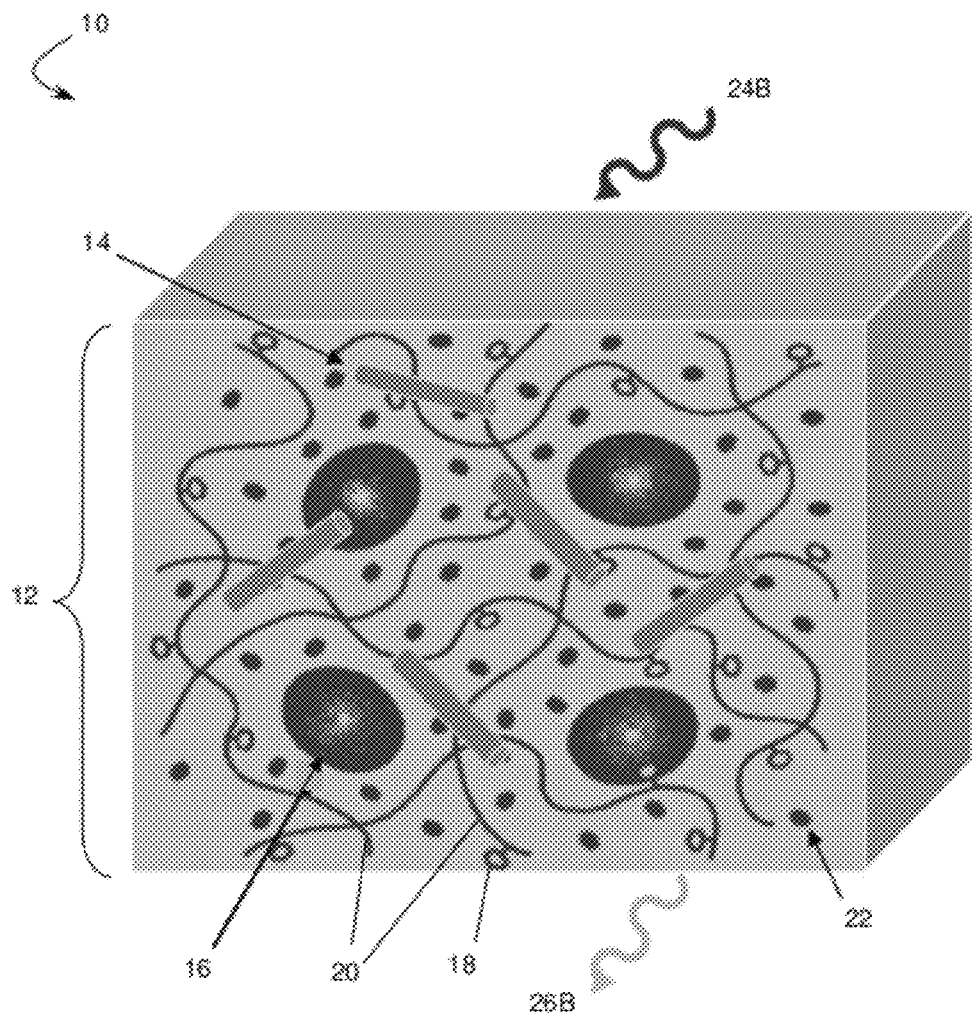

A variety of stimuli can be used to alter a property of the hydrogel. FIGS. 1-2 include exemplary schematic illustrations of a composition 10 according to one set of embodiments. FIG. 1 includes hydrogel matrix 12 which includes photoluminescent nanostructures 14. In addition, the hydrogel matrix includes binding entities 16 which are capable of binding to one or more side-groups 18 attached to the polymer chains 20 of the hydrogel. In some embodiments, side-groups 18 correspond to a target analyte. For example, polymer side-groups 18 may include various analytes such as, for example, glucose, insulin, antibodies, antigens, or any other compound one may desire to determine. In some cases, binding entities 16 may include proteins, antibodies, aptamers, boronic acids, or other entities capable of binding with side-groups 18. As shown in FIG. 1, the binding entities may bind to the side-groups of the hydrogel. The binding between the binding entities and the side-groups may lead to a relatively large amount of cross-linking between polymer chains of the hydrogel, compared to the amount of cross-linking that would be present in the absence of available binding sites on the binding entities. The relatively large amount of cross-linking may produce a composition that is relatively small in volume (i.e., shrunken) compared to one that is cross-linked to a lesser degree. As incident electromagnetic radiation 24A interacts with the photoluminescent nanostructures, a first emission of radiation 26A is produced.

FIG. 2 includes an exemplary schematic illustration of a composition 10 in the presence of excess analyte. As analyte 22 (e.g., free glucose from a blood stream) is introduced to the system, the binding entities 16 may bind with the analyte 22 rather than the side-groups 18 of polymer chains 20. This may cause the hydrogel to swell. In response to the swelling, the photoluminescence of the photoluminescent nanostructures 14 may shift. As incident electromagnetic radiation 24B interacts with the photoluminescent nanostructures in the relatively swollen composition, a second emission of radiation 26B is produced, which is substantially different from first emission 26A. Not wishing to be bound by any theory, the shift in the photoluminescence of the nanostructures may be due to a change in the local dielectric constant in the vicinity of the nanostructures.

As a specific example, in some embodiments, a composition may include a hydrogel and single-walled carbon nanotubes functioning as the photoluminescent nanostructures 14. Glucose may be attached to the polymer chains of the hydrogel, functioning as side-groups 18. Binding entities 16, suspended in the composition, may comprise glucose binding molecules such as glucose-binding proteins or boronic acid. In the absence of excess glucose, the composition may be relatively small in volume. In such a state, incident electromagnetic radiation may interact with the single-walled carbon nanotubes to produce a first emission of electromagnetic radiation.

When excess glucose is introduced into the system (e.g., from a blood stream of a patient), the glucose binding molecules may bond to the excess glucose rather than to the glucose immobilized on the polymer chains of the hydrogel. This may cause the composition to swell as the polymer chains of the hydrogel are cross-linked to a lesser extent. Upon swelling of the composition, the fluorescence emission maximum of the single-walled carbon nanotubes may shift.

Figure 13A:
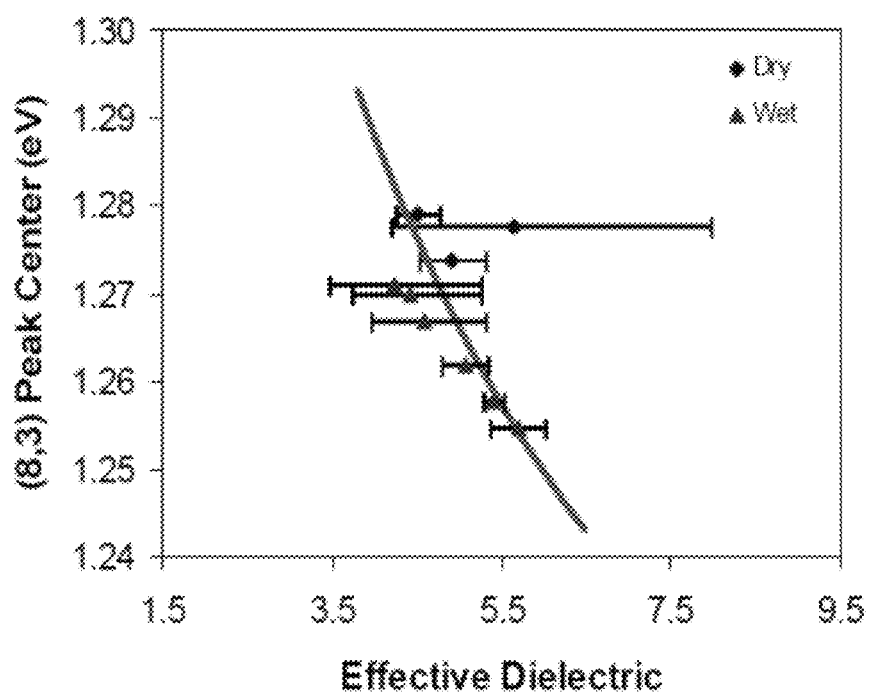
Figure 13B:
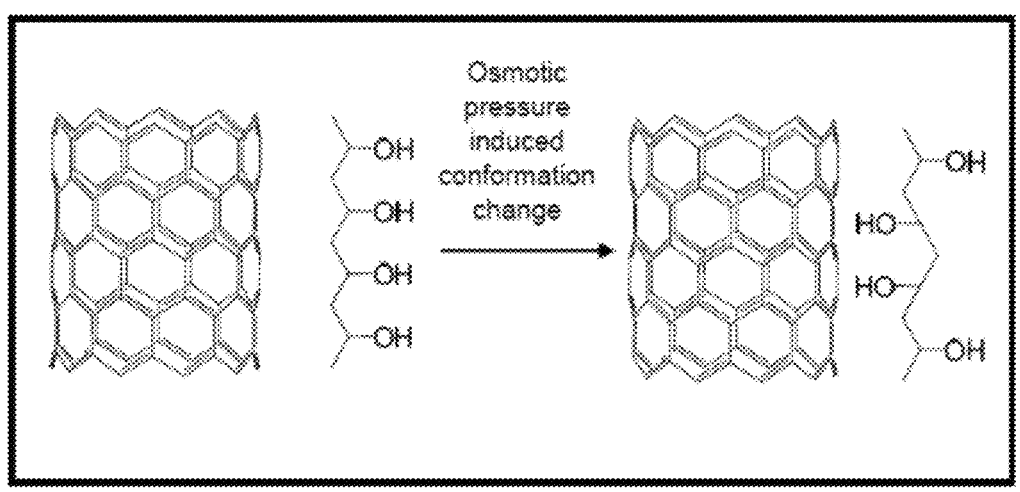

Not wishing to be bound by any theory, in some embodiments, changes in cross-linking density of the hydrogel, which may simultaneously change the internal osmotic pressure, may cause a polymer conformational change on the photoluminescent nanostructure surface. In some instances, this may produce a change in the local dielectric, and a shift in photoluminescent behavior of the nanostructure. As an example, in one set of embodiments in which poly(vinyl alcohol) is used as the hydrogel polymer and single-walled carbon nanotubes are used as the photoluminescent nanostructures, free OH groups on the PVA may be forced to associate with the surface of the single-walled carbon nanotubes (e.g., as shown in FIG. 13B) resulting in a change of the local dielectric and a shift in the emission energy of the single-walled carbon nanotubes.

While glucose has been mentioned as the analyte in this example, other analytes may be used in other embodiments. The analyte may include any suitable biochemical such as, for example, glutathione, proteins (e.g., insulin), NAD, beta-estradiol, or the like. In some embodiments, the analyte may include an antigen such as, for example, prostate specific antigen, or the like. The analyte may also include, in some embodiments, an antibody.

Non-limiting examples of analytes that can be determined using the compositions and methods described herein include specific proteins, viruses, hormones, drugs, nucleic acids and polysaccharides; specifically antibodies, e.g., IgD, IgG, IgM or IgA immunoglobulins to HTLV-I, HIV, Hepatitis A, B and non A/non B, Rubella, Measles, Human Parvovirus B19, Mumps, Malaria, Chicken Pox or Leukemia; human and animal hormones, e.g., thyroid stimulating hormone (TSH), thyroxine (T4), luteinizing hormone (LH), follicle-stimulating hormones (FSH), testosterone, progesterone, human chorionic gonadotropin, estradiol; other proteins or peptides, e.g. troponin I, c-reactive protein, myoglobin, brain natriuretic protein, prostate specific antigen (PSA), free-PSA, complexed-PSA, pro-PSA, EPCA-2, PCADM-1, ABCA5, hK2, beta-MSP (PSP94), AZGP1, Annexin A3, PSCA, PSMA, JM27, PAP; drugs, e.g., paracetamol or theophylline; marker nucleic acids, e.g., PCA3, TMPRS-ERG; polysaccharides such as cell surface antigens for HLA tissue typing and bacterial cell wall material. Chemicals that may be detected include explosives such as TNT, nerve agents, and environmentally hazardous compounds such as polychlorinated biphenyls (PCBs), dioxins, hydrocarbons and MTBE. Analytes may be detected in a wide variety of sample types, including a liquid sample or solid sample, a biological fluid, an organism, a microorganism or medium containing a microorganism, an animal, a mammal, a human, a cell line or medium containing a cell line. Typical sample fluids include physiological fluids such as human or animal whole blood, blood serum, blood plasma, semen, tears, urine, sweat, saliva, cerebro-spinal fluid, vaginal secretions; in-vitro fluids used in research or environmental fluids such as aqueous liquids suspected of being contaminated by the analyte. In some embodiments, one or more of the above-mentioned reagents is stored in a channel or chamber of a fluidic device prior to first use in order to perform a specific test or assay. In some embodiments, the sample can be cancer cells. In other embodiments, the sample can be fermentation cells, incubation cells, generation cells, or biofuel cells.

The stimuli used in association with the embodiments described herein are not limited to exposure to an analyte. In some embodiments, the stimulus may include a change in temperature, a change in pH, or a change in the wavelength and/or intensity of electromagnetic radiation. Temperature-, pH-, and light-sensitive hydrogels are known, and one of ordinary skill in the art would be able to select an appropriate hydrogel for use in the embodiments described herein.

As used herein, the terms "determination" or "determining" generally refer to the analysis of a species or signal, for example, quantitatively or qualitatively (whether the species or signal is present and/or in what amount or concentration), and/or the detection of the presence or absence of the species or signals. "Determination" or "determining" may also refer to the analysis of an interaction between two or more species or signals, for example, quantitatively or qualitatively, and/or by detecting the presence or absence of the interaction. For example, the method may include the use of a device capable of producing a first, determinable signal (e.g., a reference signal), such as an electrical signal, an optical signal, or the like, in the absence of an analyte. The device may then be exposed to a sample suspected of containing an analyte, wherein the analyte, if present, may interact with one or more components of the device to cause a change in the signal produced by the device. Determination of the change in the signal may then determine the analyte.

Specific examples of determining a species or signal include, but are not limited to, determining the presence, absence, and/or concentration of a species, determining a value or a change in value of a wavelength or intensity of electromagnetic radiation (e.g., a photoluminescence emission), determining the temperature or a change in temperature of a composition, determining the pH or a change in pH of a composition, and the like.

Nanostructures described herein may have, in some cases, a maximum cross-sectional dimension of less than about 1 less than about 500 nm, less than about 250 nm, less than about 100 nm, less than about 75 nm, less than about 50 nm, less than about 25 nm, less than about 10 nm, or, in some cases, less than about 1 nm. As used herein, the "maximum cross-sectional dimension" refers to the largest distance between two opposed boundaries of an individual structure that may be measured.

As used herein, the term "nanotube" is given its ordinary meaning in the art and refers to a substantially cylindrical molecule or nanostructure comprising a fused network of primarily six-membered rings (e.g., six-membered aromatic rings). In some cases, nanotubes may resemble a sheet of graphite formed into a seamless cylindrical structure. It should be understood that the nanotube may also include rings or lattice structures other than six-membered rings. Typically, at least one end of the nanotube may be capped, i.e., with a curved or nonplanar aromatic group. Nanotubes may have a diameter of the order of nanometers and a length on the order of millimeters, or, on the order of tenths of microns, resulting in an aspect ratio greater than 100, 1000, 10,000, or greater. In some cases, the nanotube is a carbon nanotube. The term "carbon nanotube" refers to nanotubes comprising primarily carbon atoms and includes single-walled carbon nanotubes (SWNTs), double-walled carbon nanotubes (DWNTs), multi-walled carbon nanotubes (MWNTs) (e.g., concentric carbon nanotubes), inorganic derivatives thereof, and the like. In some embodiments, the carbon nanotube is a single-walled carbon nanotube. In some cases, the carbon nanotube is a multi-walled carbon nanotube (e.g., a double-walled carbon nanotube). In some cases, the nanotube may have a diameter less than 1 μm, less than 100 nm, 50 nm, less than 25 nm, less than 10 nm, or, in some cases, less than 1 nm.

The term "quantum dot" is given its normal meaning in the art and is used to refer to semi-conducting nanostructures that exhibit quantum confinement effects. Generally, energy (e.g., light) incident upon a quantum dot will excite the quantum dot to an excited state, after which, the quantum dot will emit energy corresponding to the energy band gap between its excited state and its ground state. Examples of materials from which quantum dots can be made include PbS, PbSe, CdS, CdSe, ZnS, and ZnSe, among others.

EXAMPLES

This example describes the use of hydrogel swelling as a mechanism to reversibly induce solvatochromic shifting in single-walled carbon nanotube near-infrared emission within a biocompatible hydrogel, creating an optical sensor that reports the degree of the swelled state. Photoluminescence emission maxima from individually dispersed nanotubes in a poly(vinyl alcohol) hydrogel matrix shifted as the cross-linking was increased, with a maximum shift of −50 meV for the (6,5) nanotube. Raman scattering also shifted, with a maximum shift of up to 17 cm$^{-1}$. Not wishing to be bound by any theory, this may have been indicative of nanotube lattice strain equivalent to an effective hydrostatic pressure of about 3 GPa. The electronic band gap of a single-walled carbon nanotube was known to increase or decrease with uniaxial strain or lattice deformation due to hydrostatic pressure. Although evidence of strain was present in our system, lattice deformation did not describe the observed photoluminescence trends. Instead, a quantitative model was developed that attributed the phenomenon to changes in the local dielectric constant around the nanotube from hydrogel internal pressure and cross-linking.

The hydrogels described in this example may be useful in forming a new platform for in-vivo optical detection utilizing the tissue penetration of the near infrared emission from single-walled carbon nanotubes (SWNT). In addition, this example demonstrates that a hydrogel with immobilized apoglucose oxidase can provide real-time reversible response upon exposure to glucose.

Individually dispersed, semi-conducting single-walled carbon nanotubes (SWNT) were chosen as the photoluminescent nanostructures in this example because SWNTs exhibit near-infrared (nIR) photoluminescence (PL). The use of SWNT as near-infrared optical sensors has potential utility in clinical or medical settings because nanotube PL occurs in a region of the electromagnetic spectrum in which blood and tissue is particularly transparent. Additionally, SWNT do not photobleach and are well-suited for long-term sensing applications.

Hydrogel swelling may be caused by an osmotic pressure in its interior. The osmotic pressure can be related to the interaction between the polymer and the solvent and the number of cross-links in the hydrogel. For non-ionic hydrogels, the total internal osmotic pressure may arise from osmotic pressure due to mixing and osmotic pressure due to polymer elasticity. The total osmotic pressure driving the hydrogel swelling may be calculated as:

$$\pi = -\frac{RT}{V_1}\left[(\ln(1-\phi) + \phi + \chi\phi^2) + \frac{1}{N_c}(\phi^{1/3}\phi_0^{2/3} - \phi/2)\right] \quad [1]$$

where R is the universal gas constant, T is the temperature, $V_1$ is the molar volume of the solvent, $\chi$ is the polymer-solvent interaction parameter, $\phi$ is the polymer volume fraction, $\phi_o$ is the polymer volume fraction in the relaxed state and $N_c$ is the average number of monomers between cross-links. At equilibrium, the elastic and mixing osmotic pressures cancel, and the total osmotic pressure is equal to zero. Changing the cross-linking density also changes $N_c$ and the elastic osmotic pressure. Single-walled carbon nanotube emission energy may shift in response to lattice deformation, such as that experienced under hydrostatic pressure. In the case of uniaxial strain, the sign of emission shift is opposite for mod(n−m, 3)=2 and mod(n−m, 3)=1 nanotubes. However, SWNT PL may also be sensitive to the local environment and may shift in response to changes in the local dielectric properties.

In this example, SWNT were embedded inside a poly(vinyl alcohol) (PVA) hydrogel. As the cross-linking density and hydration state of the hydrogel are changed, the SWNT Raman scattering G-band upshifts indicating deformation of the nanotube lattice, while the SWNT PL also decreases in energy.

Figure 3:
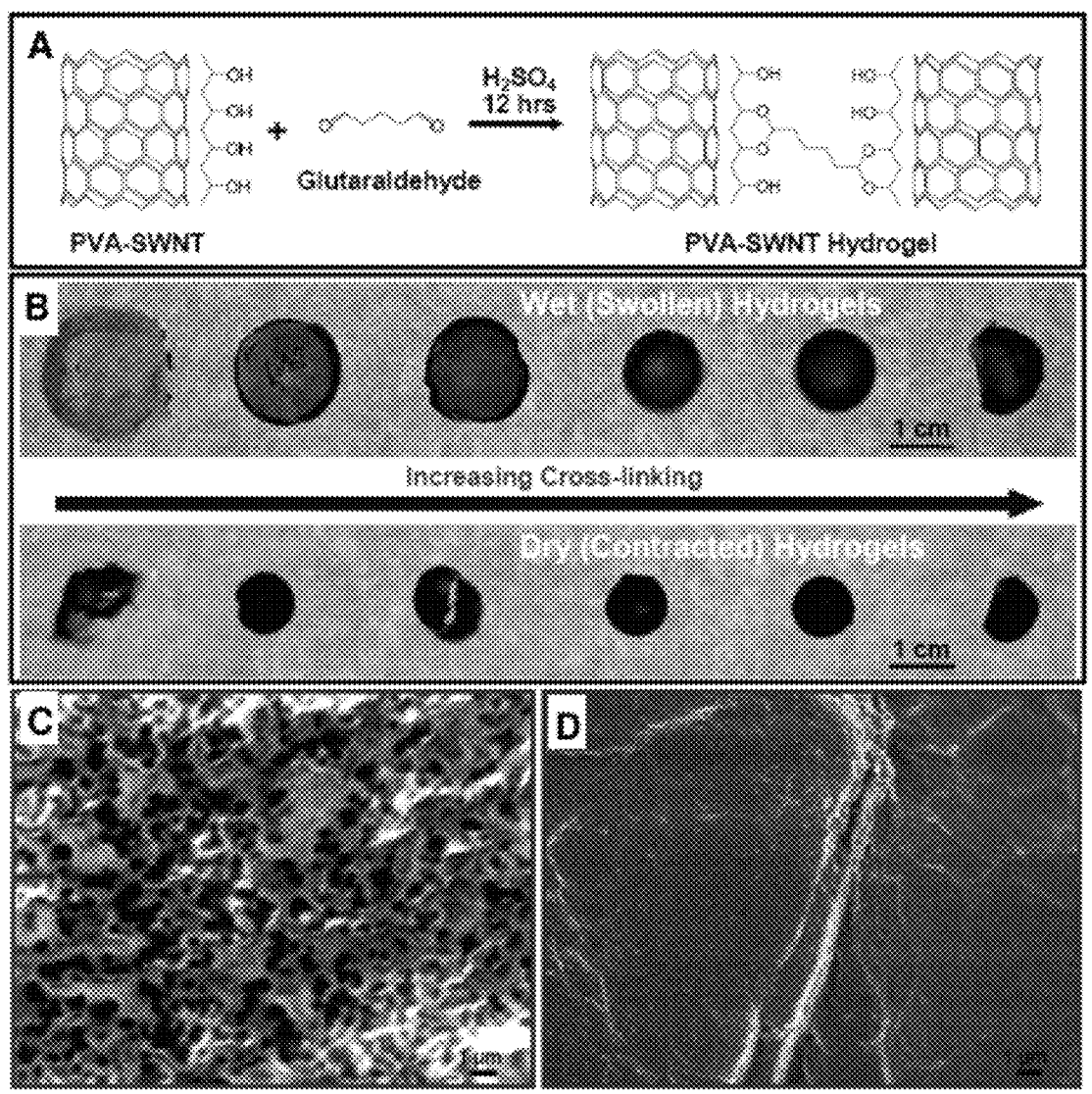
FIG. 3 includes (3A) a schematic of hydrogel formation using glutaraldehyde as the cross-linker, (3B) Poly(vinyl alcohol) hydrogels of different cross-linking densities with individually dispersed single-walled carbon nanotubes embedded inside, and (3C) and (3D) scanning electron microscopy images of compositions, according to one set of embodiments.

To embed nanotubes inside a PVA hydrogel, SWNT were suspended in PVA. Nanotubes from Southwest Nanotechnologies were suspended in a 2 wt % sodium cholate solution, which was further purified and enriched in the (6,5) nanotube using density gradient centrifugation. The resulting solutions were mixed with PVA dissolved in water to give a final PVA concentration of 5 wt %, and then dialyzed against surfactant-free buffer. Varying amounts of glutaraldehyde, the cross-linking agent, were added to the PVA-suspended nanotubes. This was followed by adding $H_2SO_4$ as the catalyst (FIG. 3A). The solutions were mixed well and then poured into Teflon molds and allowed to set for 12 hrs. The hydrogels were then washed with water until the pH of the solution was neutral and dried under vacuum until the weight of the hydrogels was constant. FIG. 3B, is a picture of SWNT-PVA hydrogels with six different cross-linking densities ranging from $N_c^{-1}$=0.003 to $N_c^{-1}$=0.123 in the swollen and dried state. In this example, $N_c^{-1}$ corresponds to the inverse of the average number of monomers between cross-links and is unitless, and may be used as a measure of hydrogel cross-linking. For simplicity, it was assumed that all of the glutaraldehyde was reacted to form cross-links within the hydrogel. The size of the hydrogel decreased with increasing cross-linking for hydrogels in the wet state. The hydrogel with the lowest cross-linking density showed the largest volume change upon swelling, as expected, and was the most deformed in the dry state. Scanning electron micrographs of the dried hydrogel (FIGS. 3C-3D) showed significant differences in the microstructure of the gel as the cross-linking was increased. Hydrogels with lower cross-linking densities exhibited visible pores in the gel structure (FIG. 3C), while higher cross-linked hydrogels exhibited no visible pore structure and appeared as a continuous surface (HG. 3D).

Figure 4A:
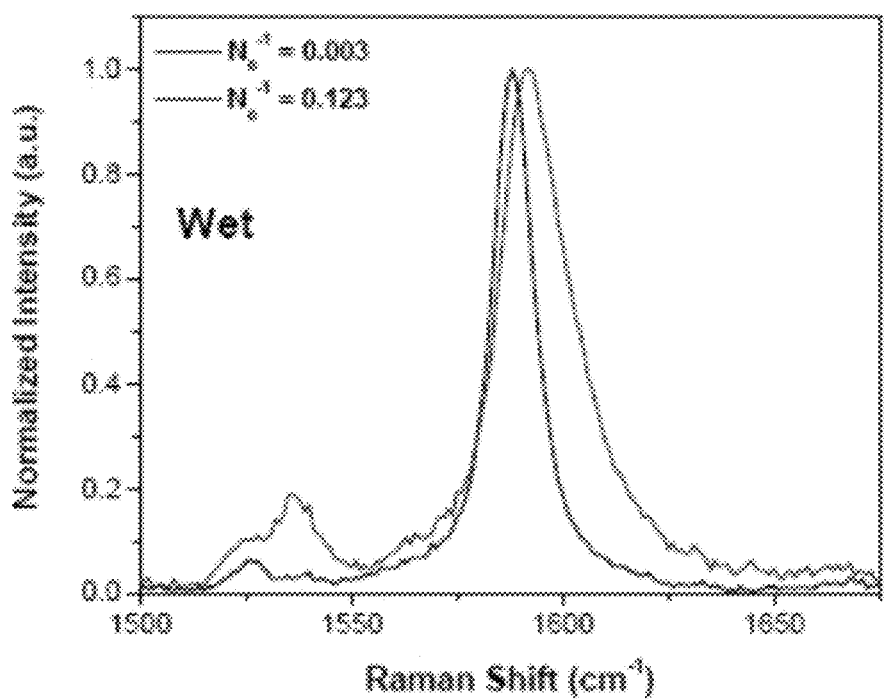
FIGS. 4-5 include (4A) and (5) plots illustrating Raman G-band shifts of the single-walled carbon nanotubes ("SWNT"), and (4B) a plot of $(\omega-\omega_o)/\omega_o$ and the calculated pressure felt by the nanotubes as a function of $N_c^{-1}$, according to one set of embodiments.
Figure 4B:
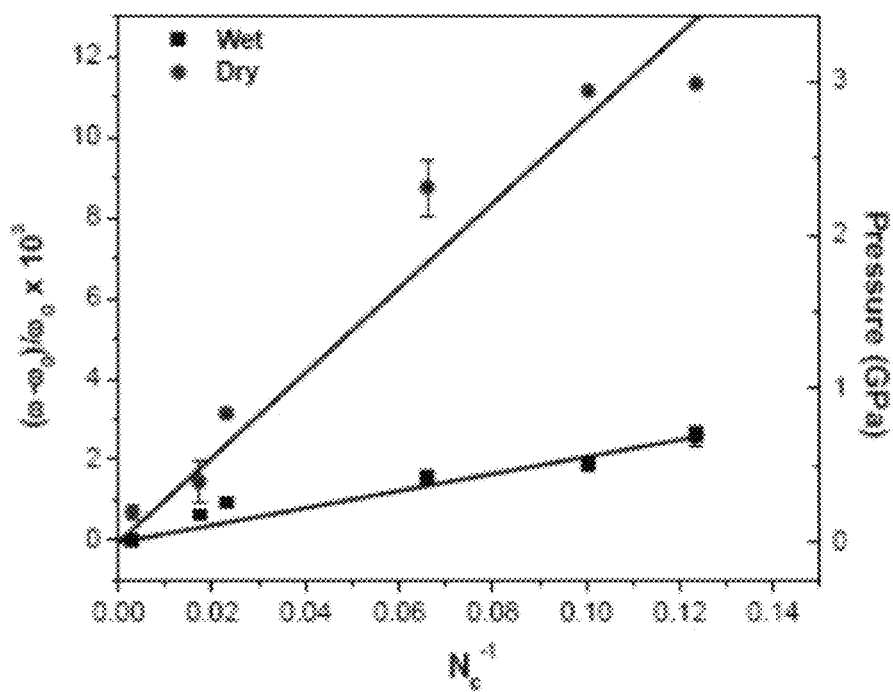

Raman scattering frequencies from SWNT inside the hydrogel upshifted with increasing hydrogel cross-linking densities and hydration state. FIG. 4A shows the Raman G-band at 785 nm excitation from wet hydrogels with cross-linking densities of $N_c^{-1}$=0.003 and $N_c^{-1}$=0.123. There was a 4 cm$^{-1}$ upshift as cross-linking was increased for the G-bands shown in FIG. 4A. A similar shift was seen for hydrogels in the dry state, with a maximum observed shift of almost 17 cm$^{-1}$. A plot of the shift in Raman frequency, normalized by the PVA-SWNT solution G-band frequency (shown as $(\omega-\omega_o)/\omega_o$), versus cross-linking is shown in FIG. 4B.

Figure 5:
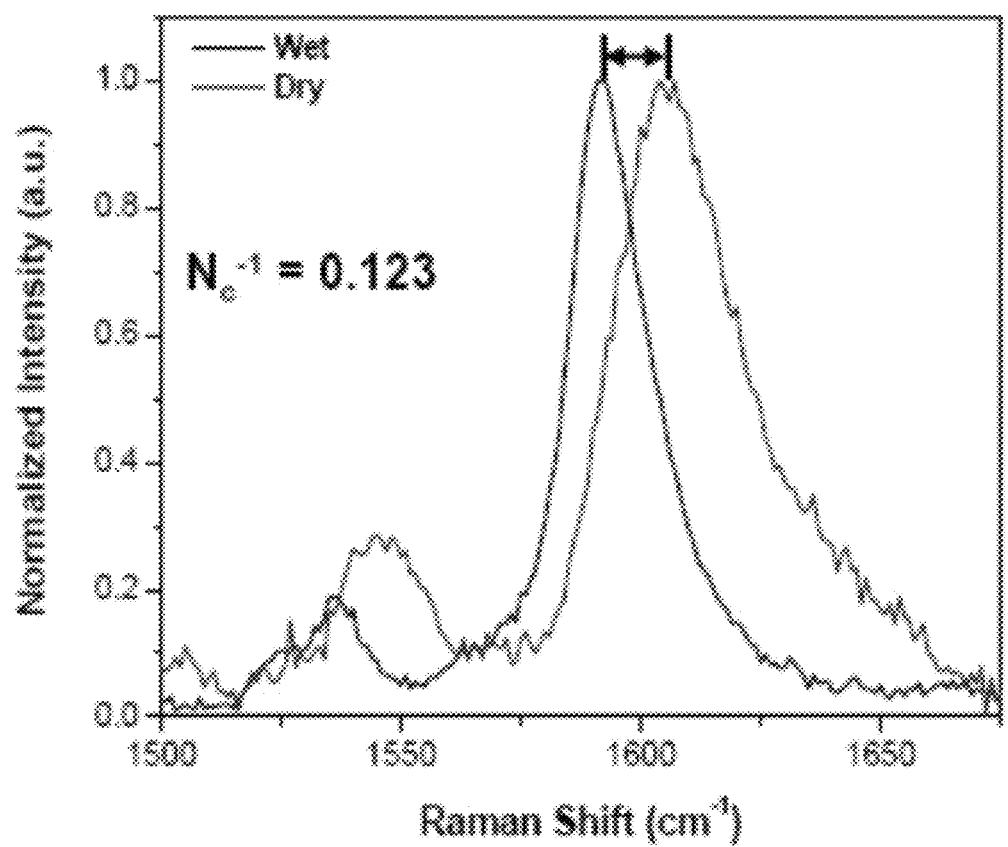

Shifts in Raman frequency of the G-band for SWNT can occur due to deformation of the SWNT lattice structure, where strain in the lattice can either result in a lengthening or shortening of the carbon-carbon bond. Not wishing to be bound by any theory, the upshift in frequency observed here may have been due to a shortening of the carbon-carbon bond as though the nanotube was experiencing a hydrostatic pressure. Using the relation of 3.8 GPa/frequency shift, an effective pressure felt by the carbon nanotube was calculated, shown on the right axis in FIG. 4B. There was further shifting of the G-band frequency as the hydrogel was dried. For a hydrogel with $N_c^{-1}=0.123$, a shift of 14 cm$^{-1}$ was observed as the hydrogel transitioned from wet to dry (FIG. 5), and was equivalent to 2.3 GPa.

Figure 6:
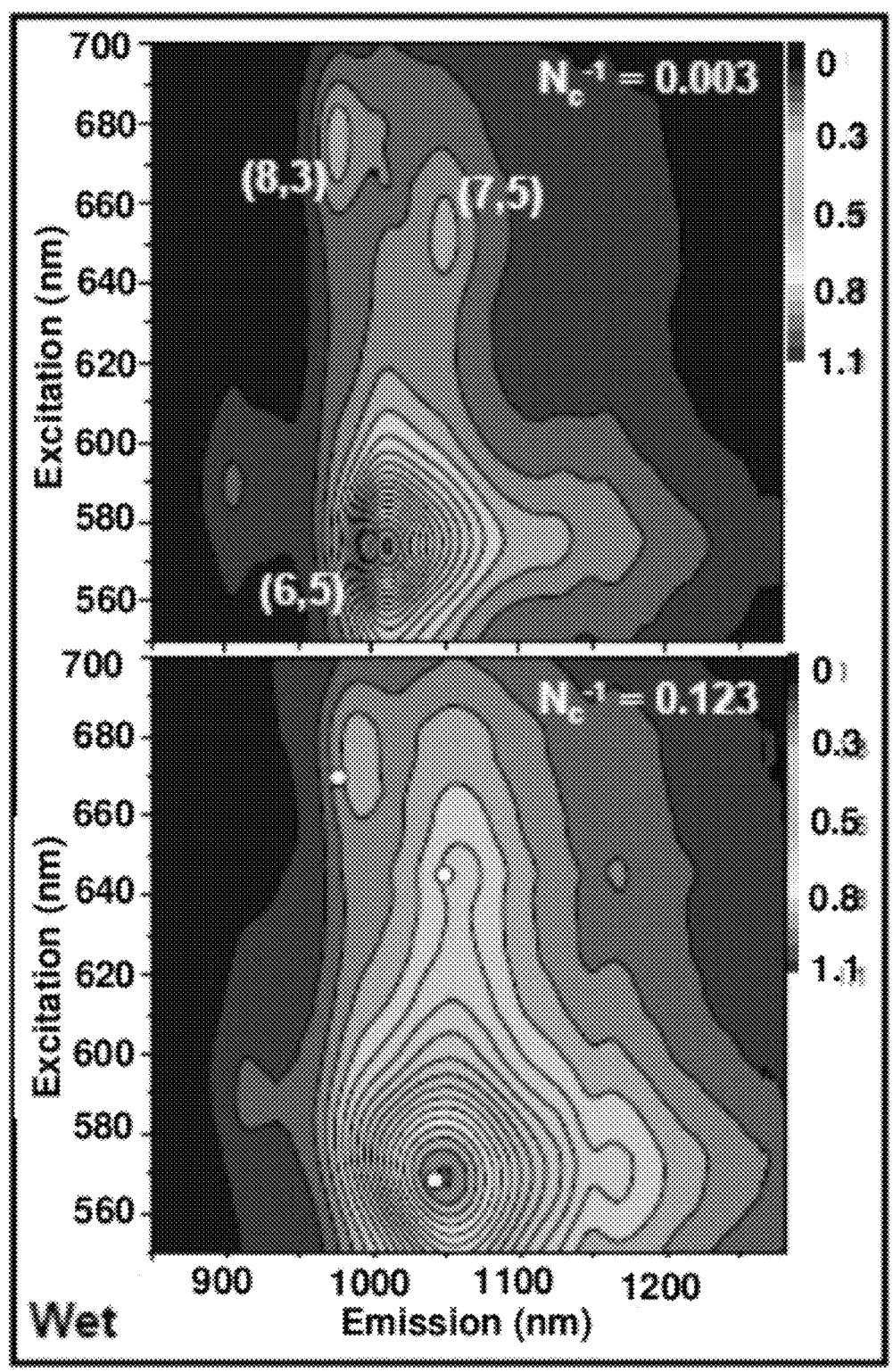
FIGS. 6-11 include (6-7) excitation-emission profiles of compositions, (8A-8B) Photoluminescence spectra of hydrogel with excitation in resonance with the (8,3) nanotube for $N_c^{-1}=0.003$ and $N_c^{-1}=0.123$ in the wet (8A) and dry (8B) state, (9A, 9B and 10A) plots of the peak centers as a function of $1/N_c$ for three nanotube species, and (10B, 11A and 11B) plots of the shifts of SWNT PL from the wet to the dry state (squares) and the modeled shifts due to strain (triangles), according to one set of embodiments.
Figure 7:
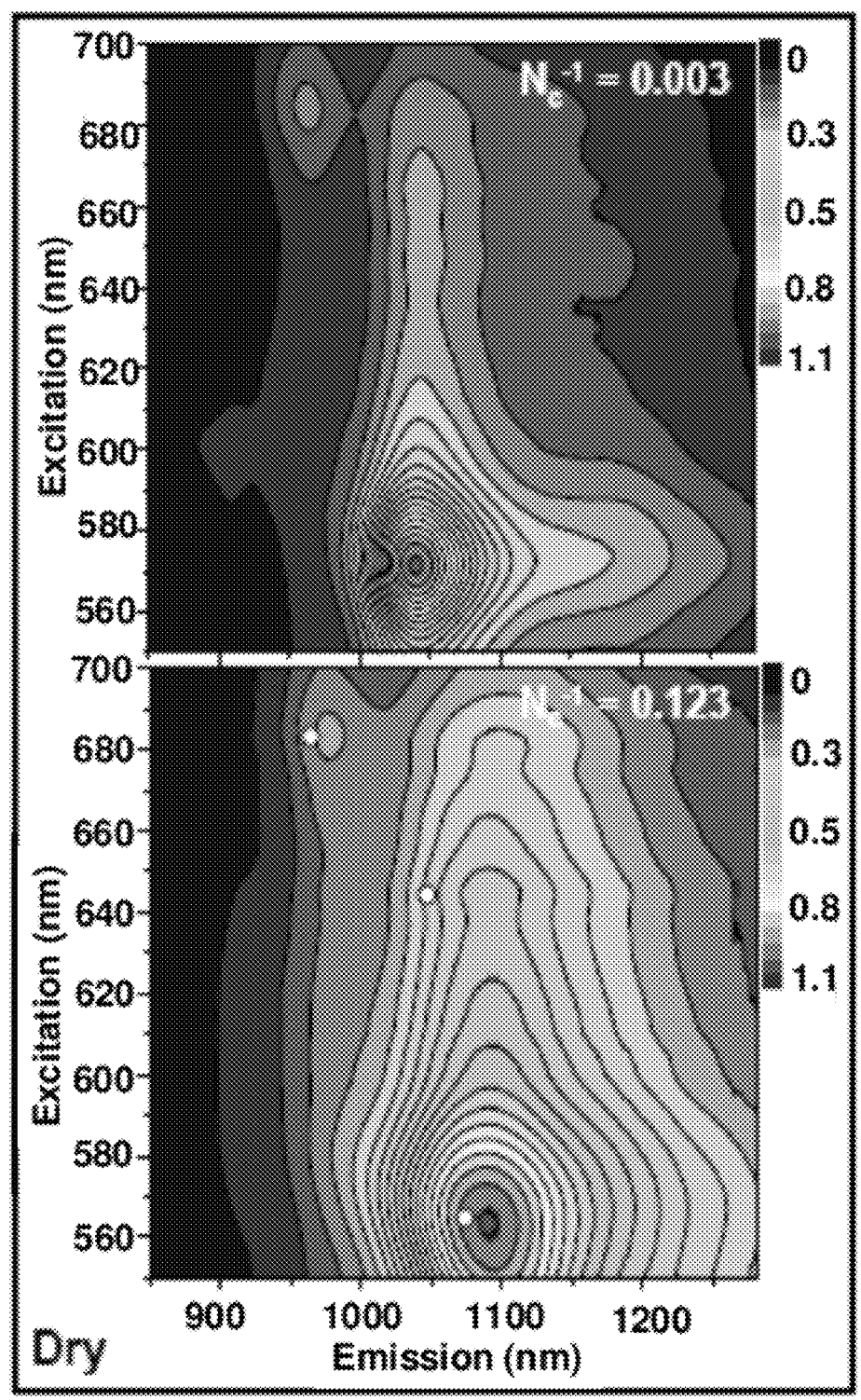
Figure 8A:
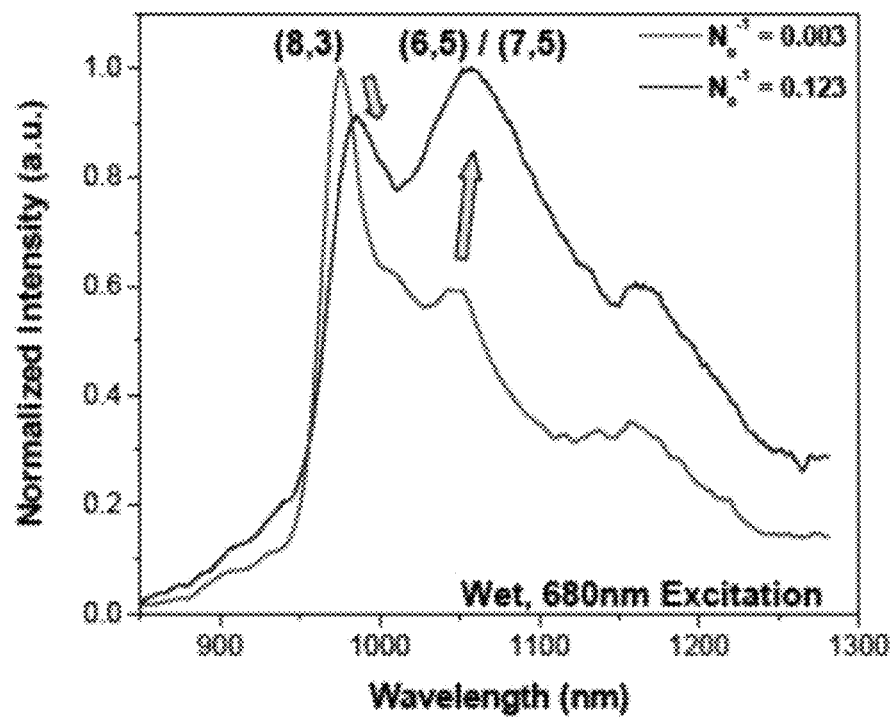
Figure 8B:
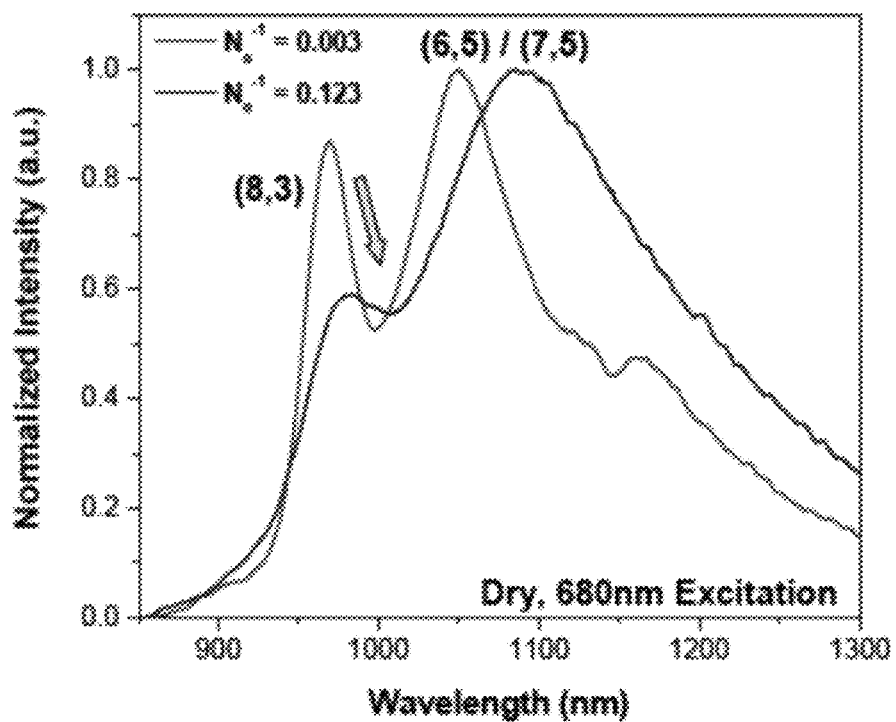
Figure 9A:
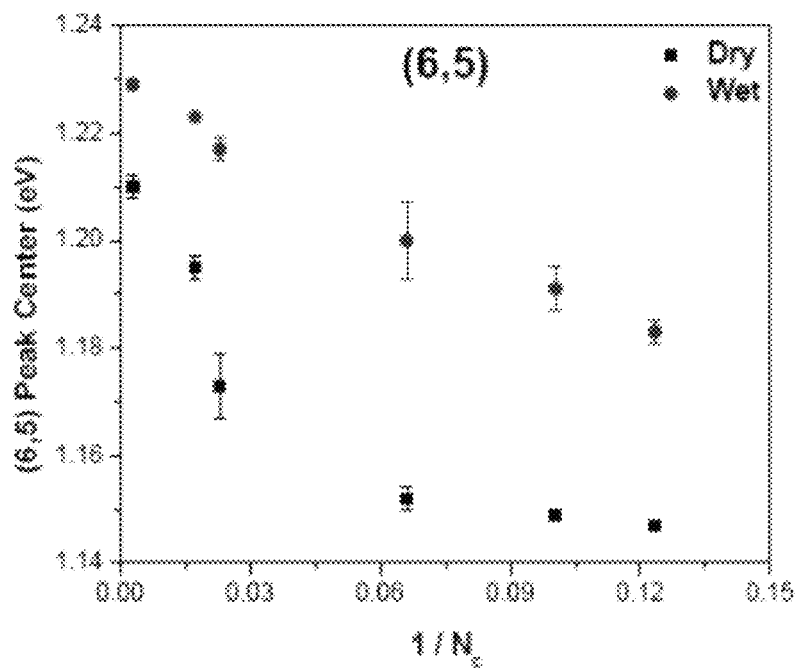
Figure 9B:
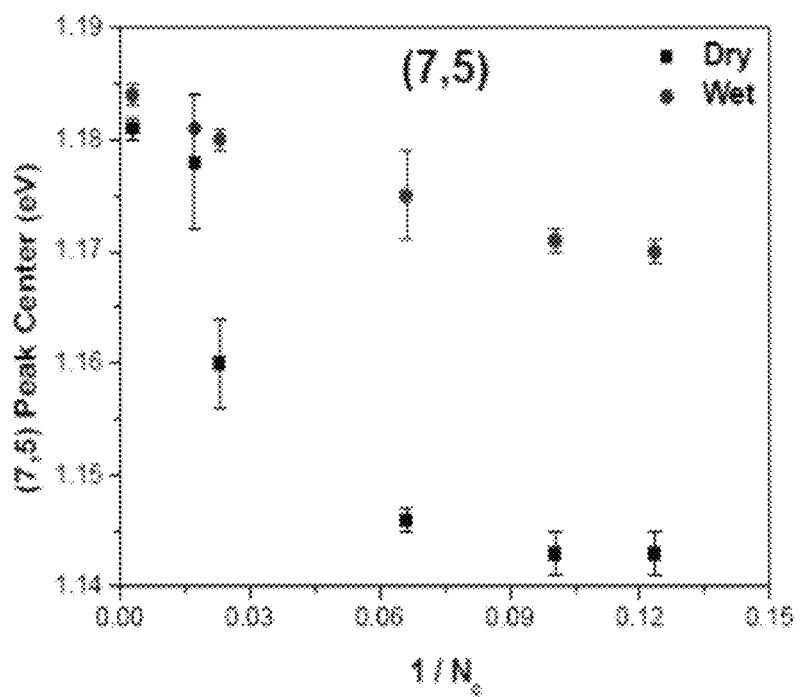
Figure 10A:
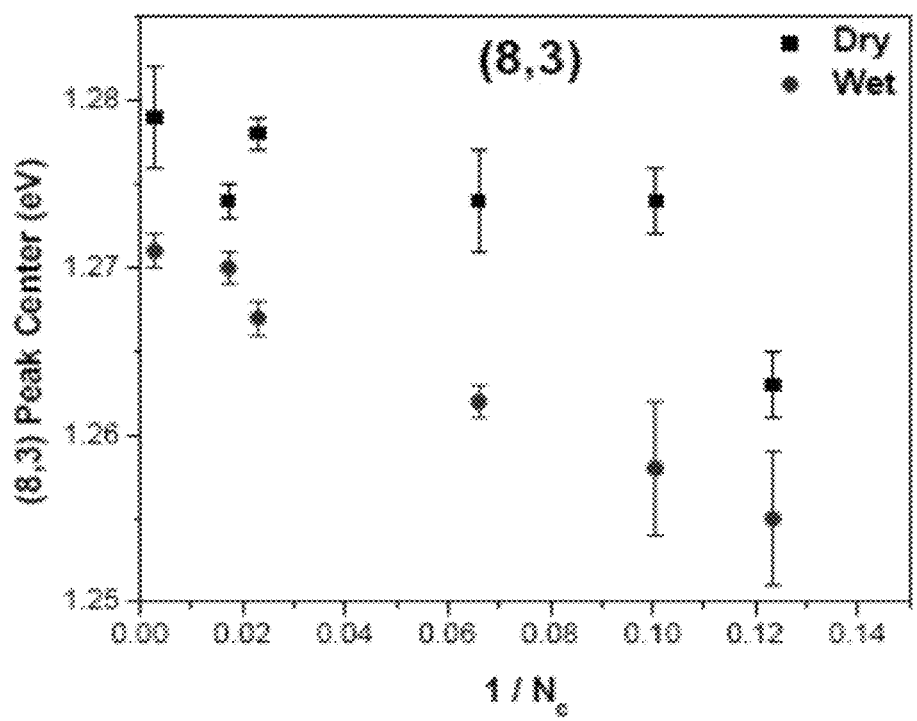

The photoluminescence emission maxima from the SWNT-PVA hydrogels also shifted depending on hydrogel cross-linking and hydration state. Nanotube emission spectra were measured using an InGaAs array coupled to an inverted Zeiss microscope. FIG. 6 shows excitation-emission profiles for the PVA-SWNT hydrogels at cross-linking densities of $N_c^{-1}=0.003$ and $N_c^{-1}=0.123$ inside wet hydrogels. As the cross-linking density was increased there was a clear red-shift in the PL emission maxima for all three nanotubes. A similar trend was observed for hydrogels in the dry state, as shown in FIG. 7. Since the (8,3) nanotube had the largest bandgap of the nanotubes in the sample, changes in the nanotube-nanotube distance, due to increases in the hydrogel cross-linking density or drying the hydrogel, may have resulted in energy transfer from the (8,3) nanotube to either the (7,5) or the (6,5) nanotubes (FIGS. 8A-8B). This effect may be seen as a decrease in the (8,3) PL intensity relative to intensities of the (6,5) and (7,5) nanotubes. FIGS. 6-7 also show significant broadening of SWNT PL as cross-linking was increased and the hydrogel was dried. Not wishing to be bound by any theory, this may be attributable to heterogeneous peak broadening due to inhomogeneous environments seen by all the nanotubes in the hydrogel. This inhomogeneity may have been localized to the nanotube itself as different spatial locations on the hydrogel did not show location-specific emission maxima. Plotting the emission peak center versus cross-linking showed an apparently linear decrease in emission energy for the (6,5), (7,5) and (8,3) nanotubes in wet hydrogels (FIGS. 9A, 9B and 10A). For the (6,5) and (7,5) nanotubes, the shift in emission maxima in the dry hydrogel appeared to reach a saturation point where further cross-linking of the hydrogel would not cause further shifting. While the emission maximum generally decreased with increased cross-linking for the (8,3) nanotube in a dry hydrogel, there was scatter in the data points. Not wishing to be bound by any theory, this may have been due to the broadening and energy transfer observed in the spectra, making it difficult to indentify exact emission maxima.

Figure 10B:
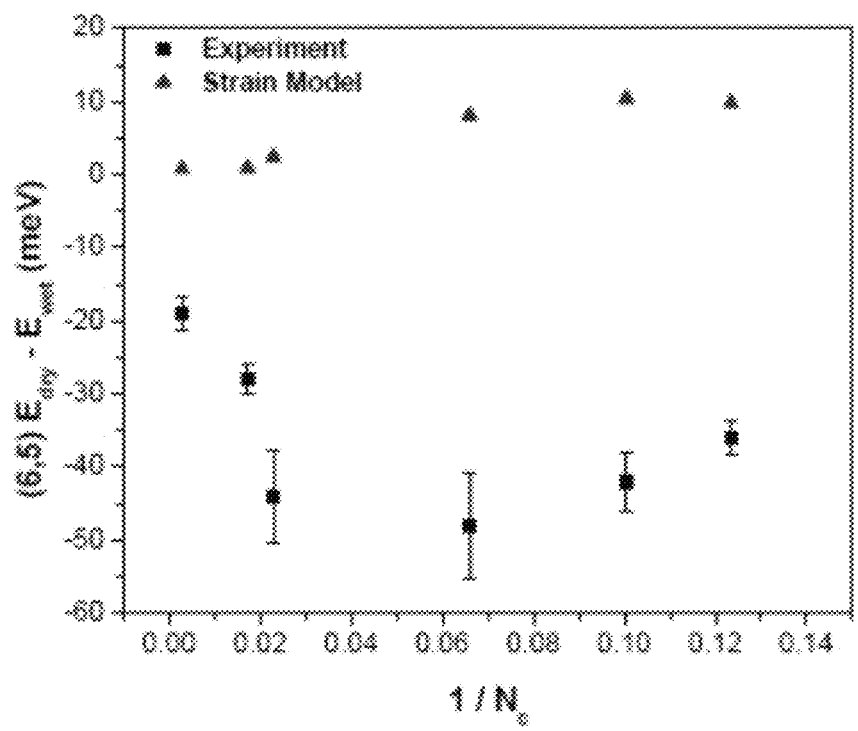
Figure 11A:
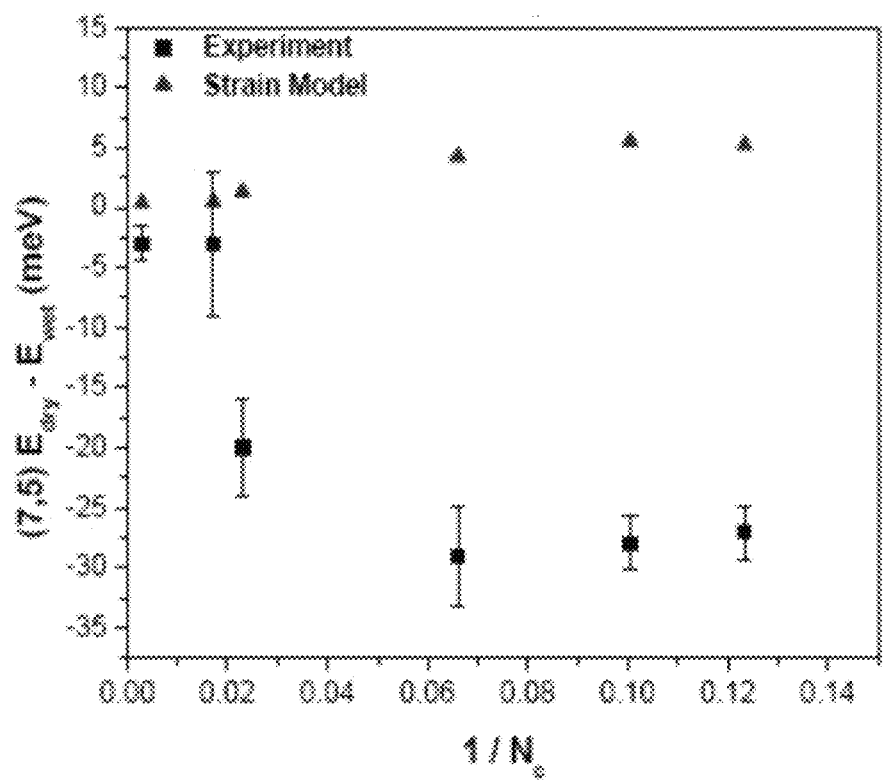
Figure 11B:
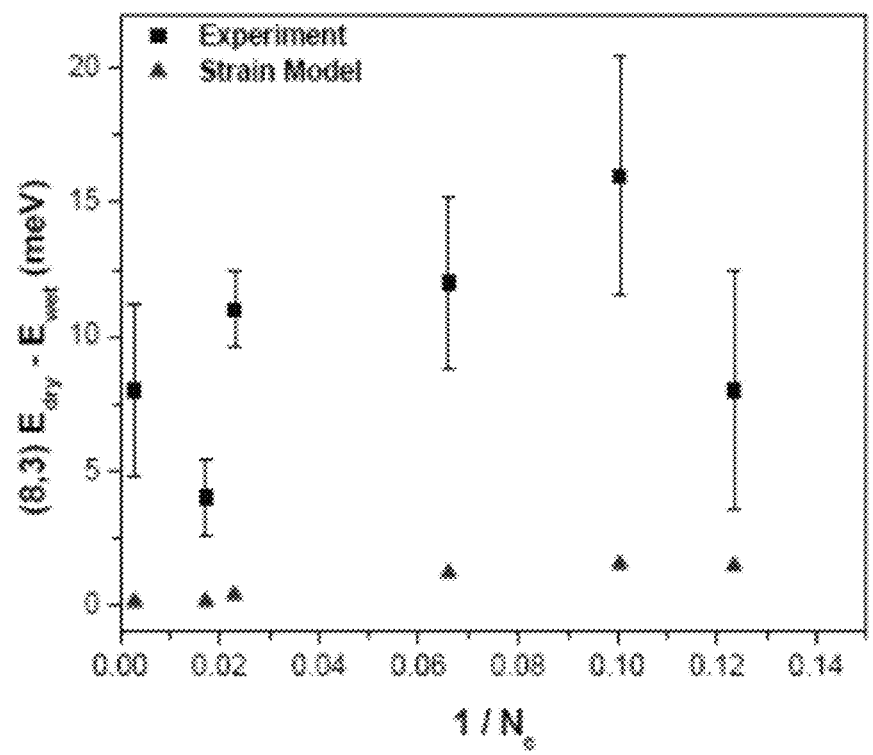

The bandgap of nanotubes experiencing lattice deformation may either increase or decrease depending on the strain and the nanotube type. The shift in band gap with radial, $\eta_r$, and axial, $\eta_z$, strain for the $E_{11}$ gap may be calculated as:

$$\Delta E_{strain} = -2E_{11}\eta_r + 3\gamma_0(-1)^q(\eta_r-\eta_z)\cos(3\theta) \quad [2]$$

where, $E_{11}$ is the bandgap in vacuum, $\gamma_o$ is the nearest neighbor electron hopping parameter (which ranges from 2.4 to 2.9 eV), q is equal to mod(n–m,3) and θ is the nanotube chiral angle. The radial and axial strain was nanotube dependent and was estimated using pressure estimates. For $\gamma_0$ a value of 2.54 eV was chosen from the literature for nanotubes under uniaxial strain, although using another value for $\gamma_0$ led to only minimal changes in the results. FIGS. 10B, 11A and 11B include plots of the shift in SWNT PL peak center versus cross-linking for the dry to wet hydrogel transition as well as the calculated shift due to strain. For all three nanotube species, the change in bandgap due to strain effects was unable to explain the observed shift in SWNT PL. For both the (6, 5) and (7, 5) nanotubes the predicted shift due to strain was of the opposite sign as the observed shift. In the case of the (8, 3) nanotube the sign of the shift was correct, but the magnitude was insufficient. Not wishing to be bound by any theory, it was determined that strain alone could not explain the observed shifts and was probably not the dominant factor.

Figure 17A:
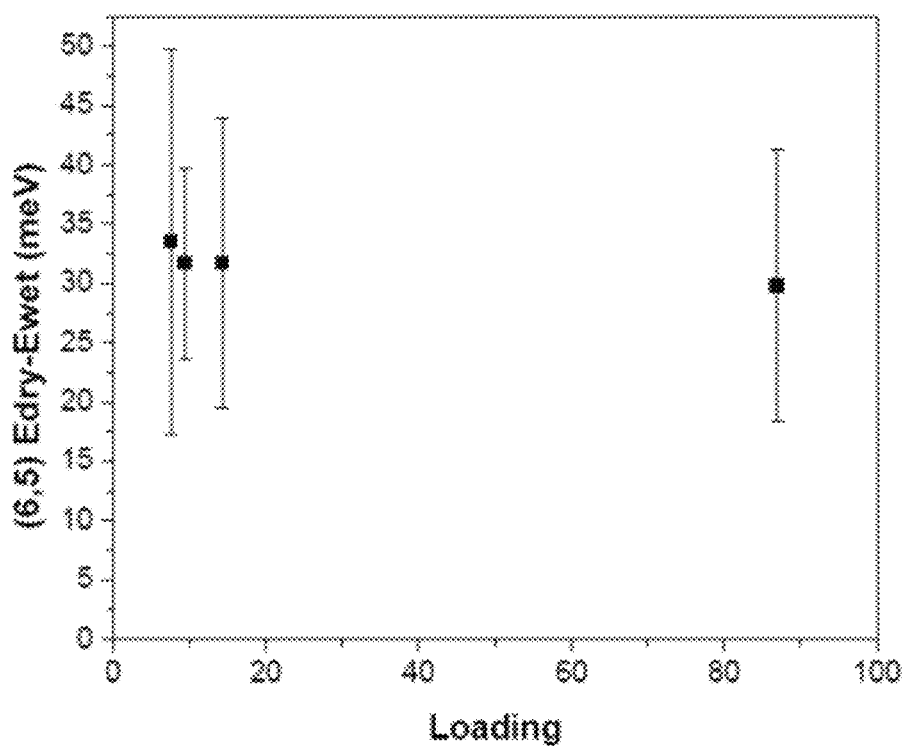
FIG. 17 includes (17A and 17B) plots of peak centers for the (6,5) and (7,5) nanotubes versus nanotube loading, according to one set of embodiments.
Figure 17B:
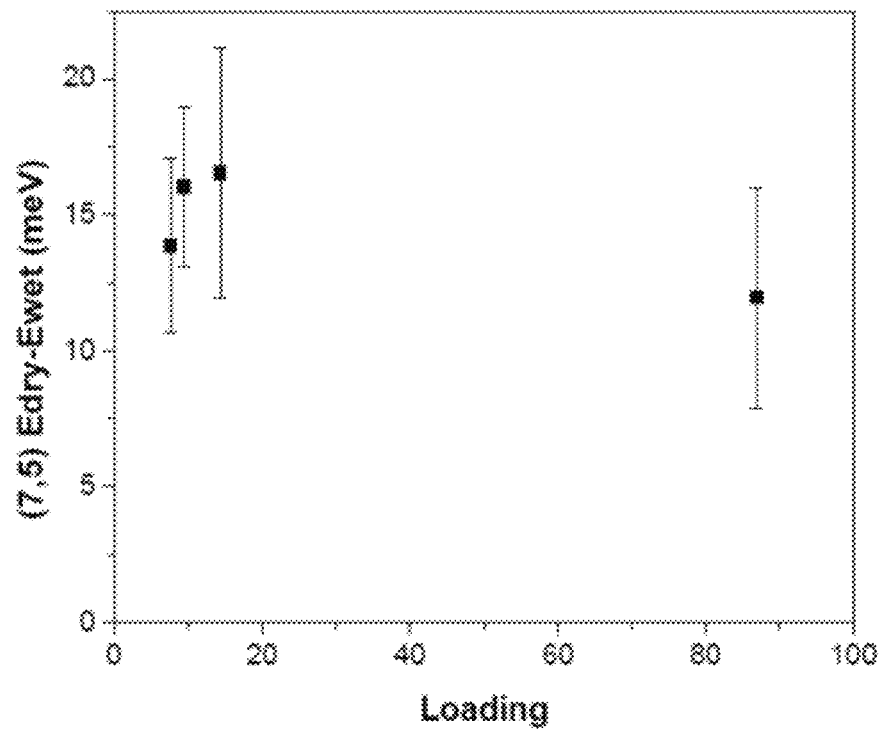

Aside from nanotube lattice deformation, several alternative hypotheses were explored. As seen in FIGS. 8A and 8B, there was exciton energy transfer between the nanotubes in the hydrogel. It was possible that part of the large shift in PL for the (6,5) nanotube was, in part, due to exciton-energy transfer to the (7,5) nanotube. This effect was expected to be very sensitive to the nanotube loading in the hydrogel, with lower loading leading to decreased energy transfer because the SWNT spacing would become too large for such effects to be prominent. However, decreasing the nanotube loading by an order of magnitude did not change the shift of the nanotube fluorescence (FIGS. 17A and 17B).

Figure 18:
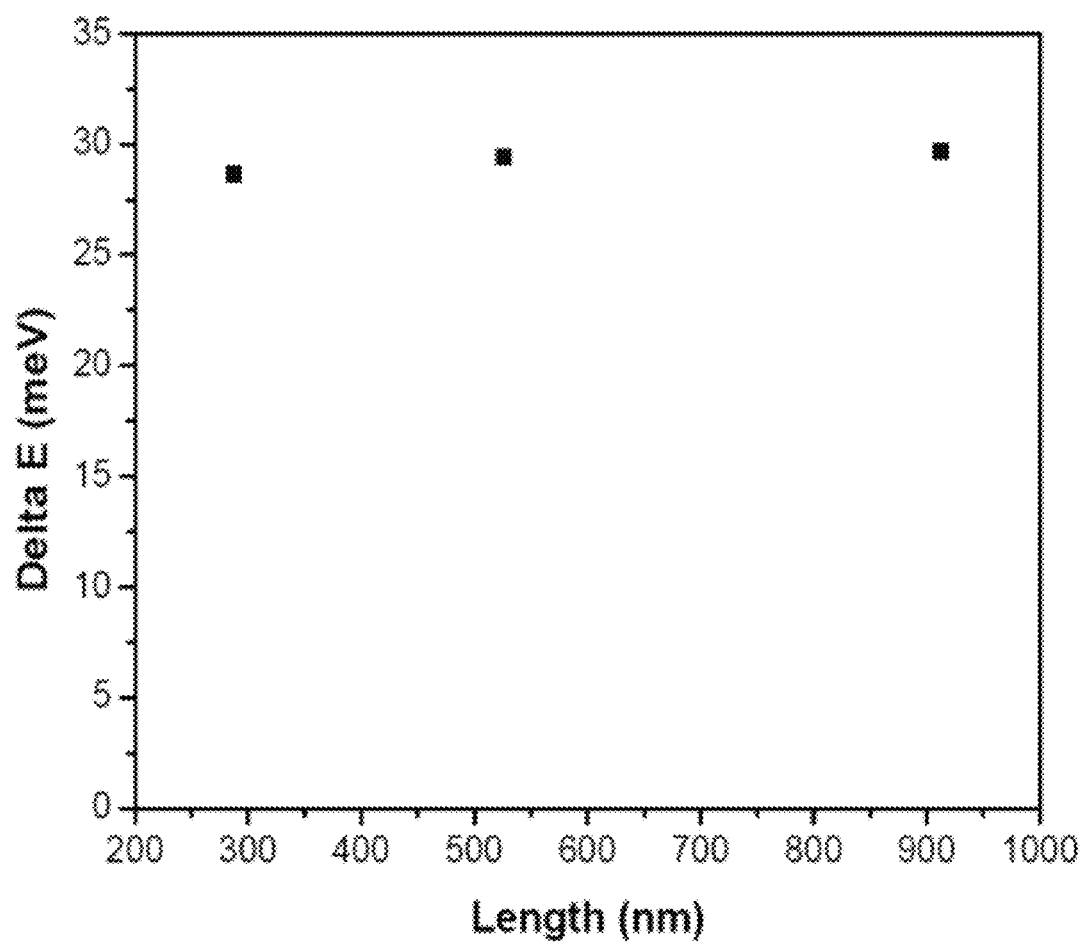
FIG. 18 includes a plot of the shift in energy of (6,5) nanotube photoluminescence peaks going from dry to wet hydrogel versus nanotube length, according to one set of embodiments.

Also explored was the possibility that SWNT length, which affected the intertube distance, contributed to the shift. In the case of long nanotubes, it was conceivable that they could be exposed to greater strain along the length of the nanotube due to polymer entanglement, yet changes in nanotube length did not cause any change in the observed shift (FIG. 18).

Additionally, the possibility that local heating of the nanotube, due to the excitation source, led to the observed shift was explored. If heating played a role, the PL shift would be commensurate for all the dried hydrogels, but because this was not the case, it was highly unlikely that this was the cause.

Figure 12A:
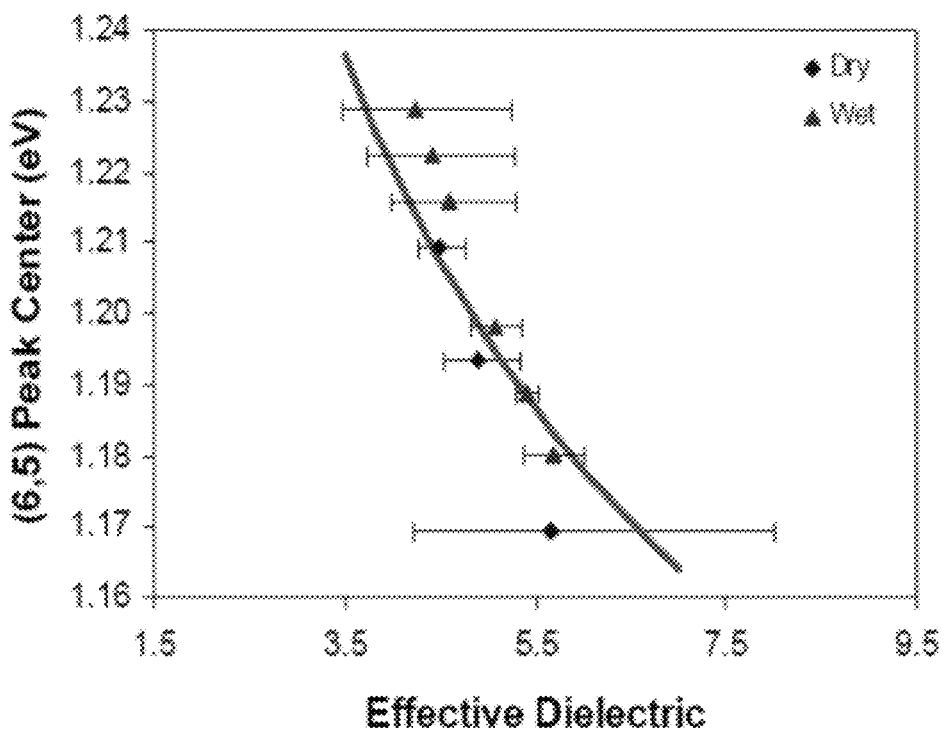
FIGS. 12-13 include (12A, 12B and 13A) plots of the peak center for the (6,5), (7,5) and (8,3) nanotube versus the calculated dielectric constant, and (13B) a schematic of the possible PVA conformational change due to changes in osmotic pressure and cross-linking, according to one set of embodiments.
Figure 12B:
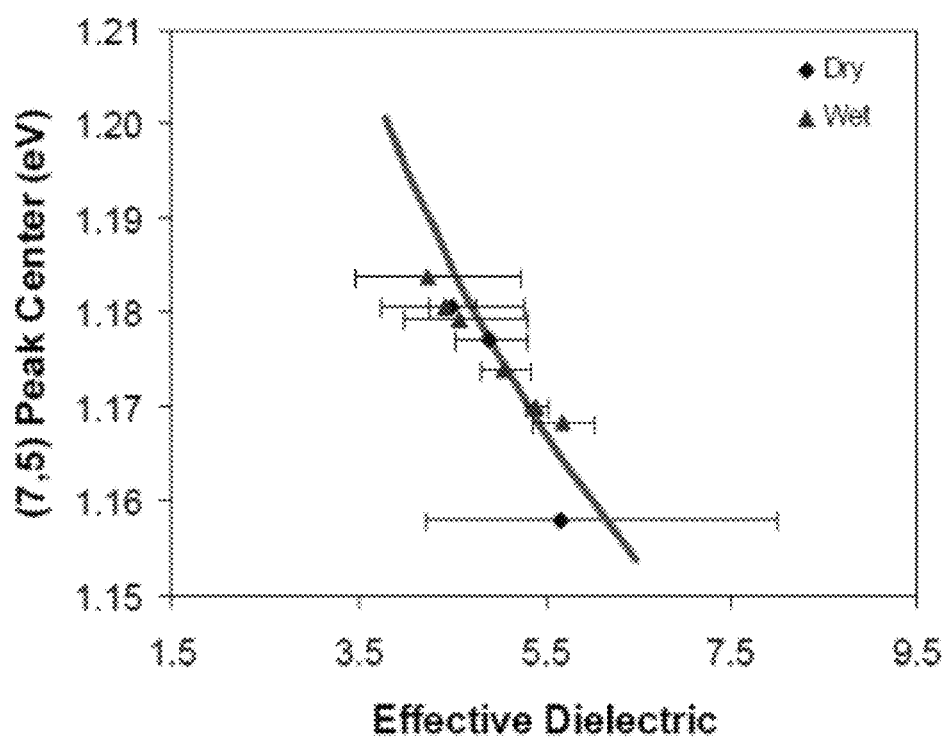
Figure 19:
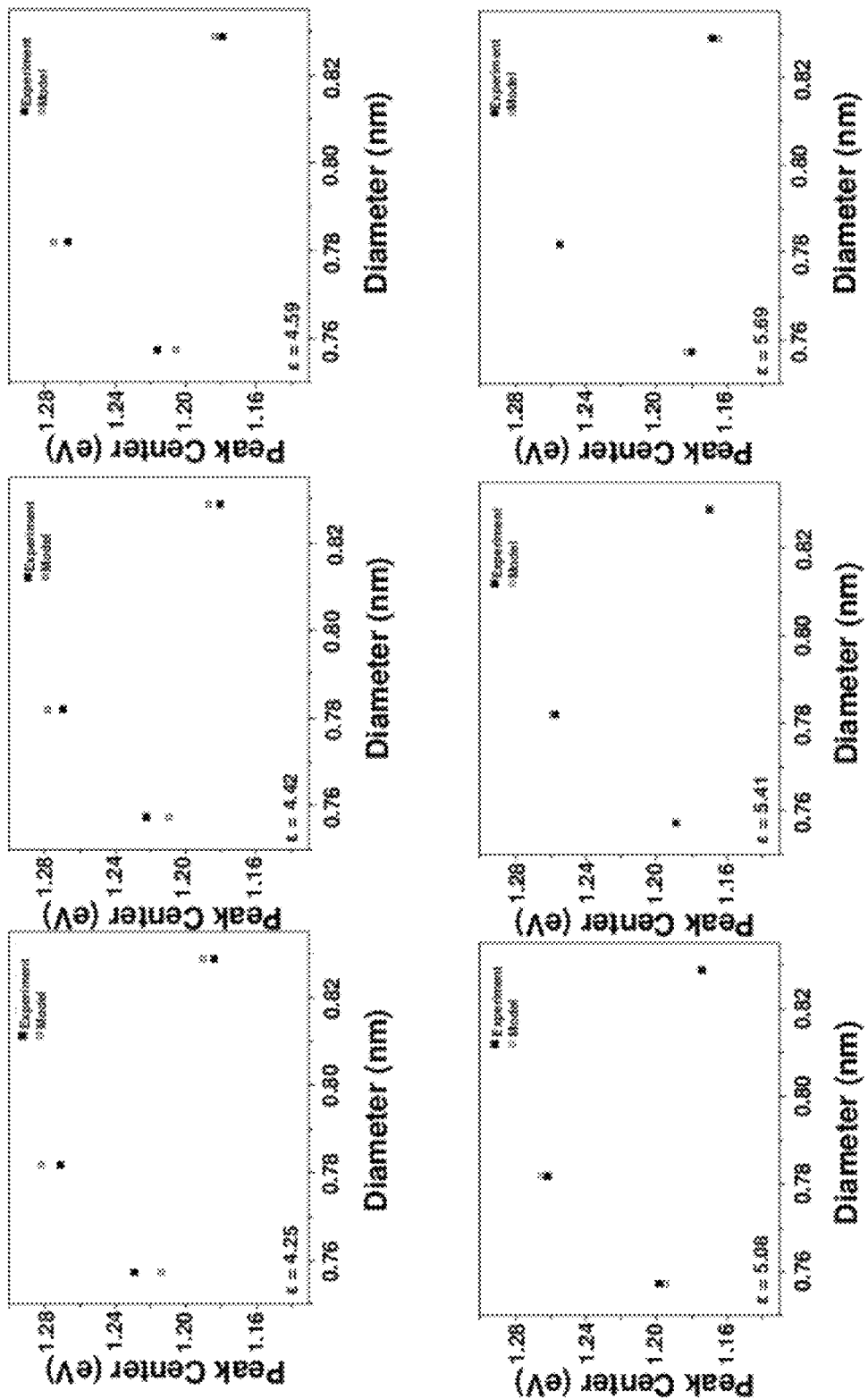
FIG. 19 includes plots of peak centers for the (8,3), (6,5) and (7,5) nanotubes, both measured and calculated from the model, shown for the 6 wet hydrogels, according to one set of embodiments.
Figure 20:
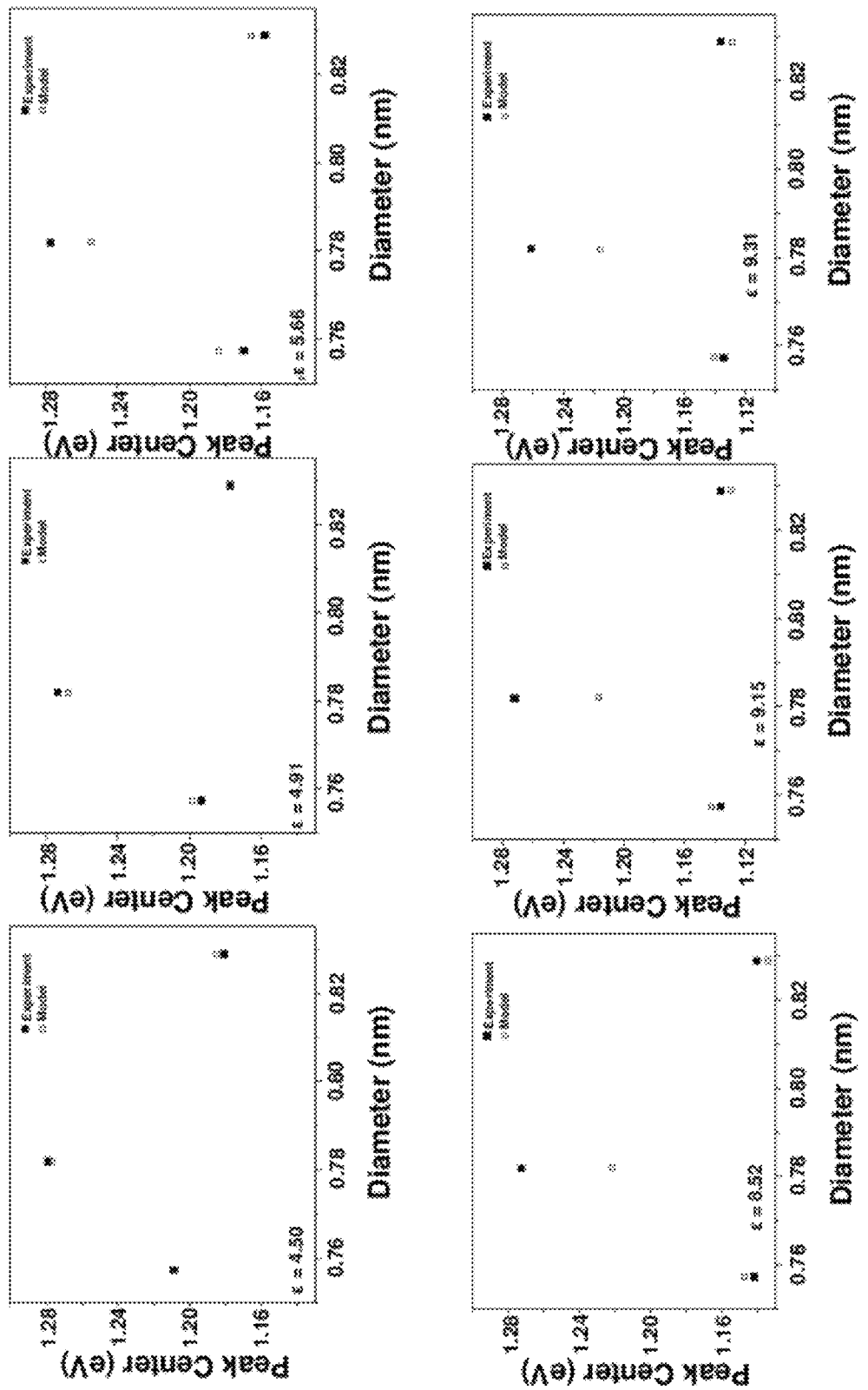
FIG. 20 includes plots of peak centers for the (8,3), (6,5) and (7,5) nanotubes, both measured and calculated from the model, shown for the 6 dry hydrogels, according to one set of embodiments.
Figure 21:
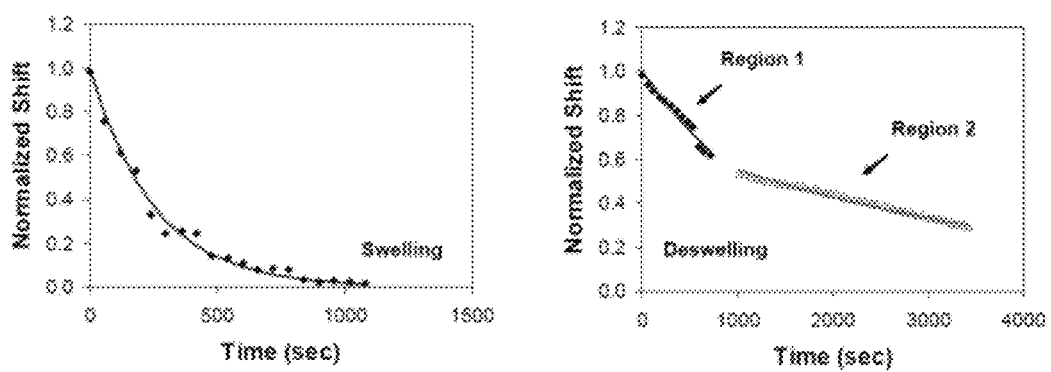
FIG. 21 includes fits of hydrogel swelling data to a first order model, according to one set of embodiments.

While it was expected that the local dielectric seen by the nanotube was different between the dry (air) and wet state, changing the cross-linking density, and thus the hydrogel osmotic pressure, could change polymer conformation and therefore the local dielectric constant seen by the nanotube. Nanotube PL is excitonic in nature, having strongly bound excitons with an exciton binding energy, $E_{bind}$, and a self-interaction energy between the excited excitonic states, $E_{SI}$. Both $E_{bind}$ and $E_{SI}$ may experience screening from the dielectric environment, causing their energies to decrease. Scaling relations of the exciton binding energy with the dielectric have been found to be $E_{bind} \propto \varepsilon^{-1.4}$ and $E_{bind} \propto \varepsilon^{-1.2}$ from the literature. Similarly, the self-interaction energy may scale inversely with the dielectric. Therefore, the shift in emission maxima to changes in the exciton binding energy and the self-interaction energy may be related as:

$$\Delta E = \Delta E_{SI} - \Delta E_{bind} + \Delta E_{strain} \quad [3]$$

with the change in self-interaction and exciton binding energies given by:

$$\Delta E_{SI} = E_{SI}^{\varepsilon=1}\left(\frac{1}{\varepsilon} - 1\right) \quad [4]$$

$$\Delta E_{bind} = E_{bind}^{\varepsilon=1}\left(\frac{1}{\varepsilon^{1.2}} - 1\right) \quad [5]$$

where $E_{SI}^{\varepsilon=1}$ and $E_{bind}^{\varepsilon=1}$ are the self-interaction and exciton binding energies in vacuum, respectively. Using the above model, a test was conducted to determine if a change in dielectric constant could self-consistently model the sign and magnitude of the observed shift for all three nanotubes reported. The following self-interaction energies were used: $ESI,(6,5)=1.954+/-0.007$ eV, $ESI,(7,5)=1.812+/-0.005$ eV and $ESI,(8,3)=1.963+/-0.007$ with the listed 99.9% confidence intervals. The corresponding exciton binding energies were 1.647 eV, 1.581 eV and 1.718 eV, respectively. Using these values, the data of each hydrogel (six cross-linking densities and two hydration states) were fit to Equation 3 by calculating the effective dielectric seen by the nanotube. The data and the calculated fits for each hydrogel are shown in FIGS. 19-20. FIGS. 12A, 12B and 13A include plots of nanotube peak center versus the dielectric constant determined from fitting each hydrogel separately, with 95% confidence intervals for each dielectric constant included. For all three nanotubes, the wet and dry hydrogel data converged to a single line. The calculated dielectrics fell within a reasonable range. In addition, assuming literature values of $\epsilon_{PVA}=6.9$, $\epsilon_{water}=1.769$, and $\epsilon_{air}\sim 1$ led to a fractional PVA coverage on the nanotube of 48% to 79%. Not wishing to be bound by any theory, it was determined that changing the cross-linking density of the hydrogel, which simultaneously changed the internal osmotic pressure, may have caused a polymer conformational change on the nanotube surface, forcing free OH groups on the PVA to associate with the nanotube surface (FIG. 13B) and resulting in a change of the local dielectric and a shift in SWNT emission energy.

Figure 14A:
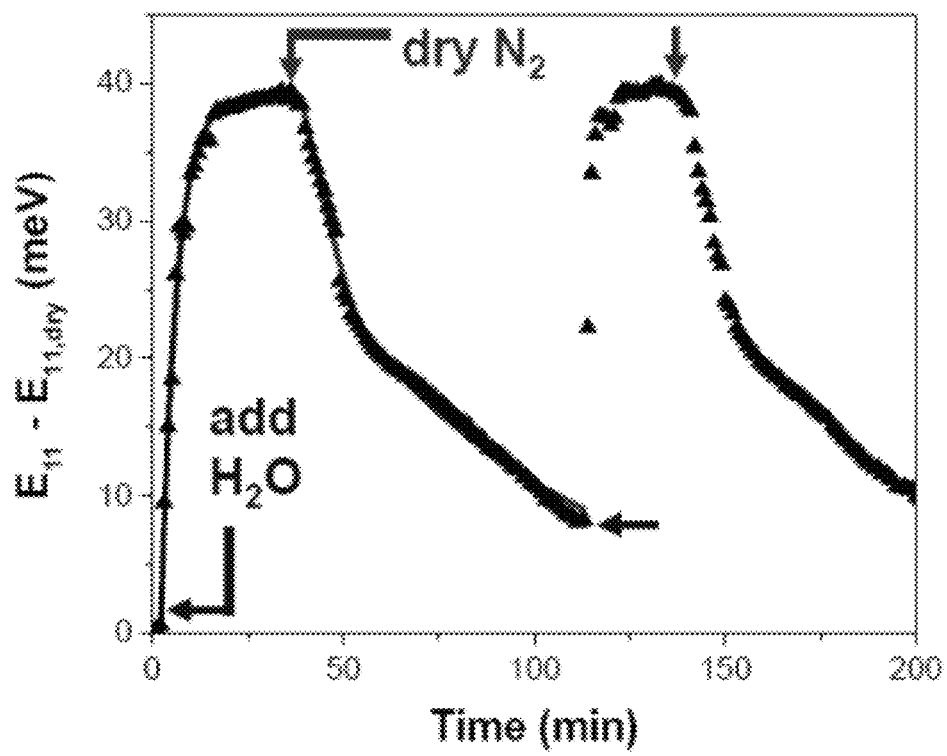
FIGS. 14-16 include (14A) a plot of $E_{11}$-$E_{11, dry}$ as a function of time, (14B) a plot of intensity as a function of wavelength, (15A) transient shift during hydrogel swelling of SWNT PL for PVA-SWNT hydrogel, with $N_c^{-1}=0.003$, implanted in mouse, reported as the intensity at 1007 nm divided by the intensity at 1026 nm with excitation from 550 to 800 nm, (15B) a picture of measurement set-up with mouse positioned on the microscope, and (16) responses of ApoGOx-attached hydrogel upon periodic exposure to glucose (G: 10 mM glucose; B: 10 mM PBS solution, pH 6.8), according to one set of embodiments.
Figure 14B:
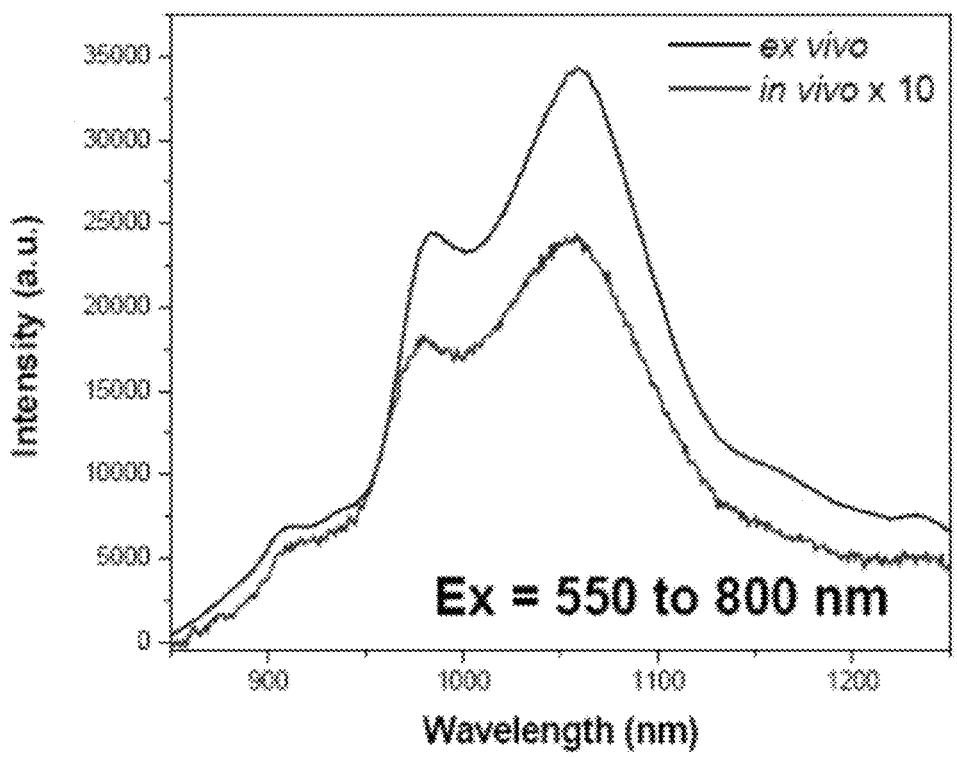
Figure 15A:
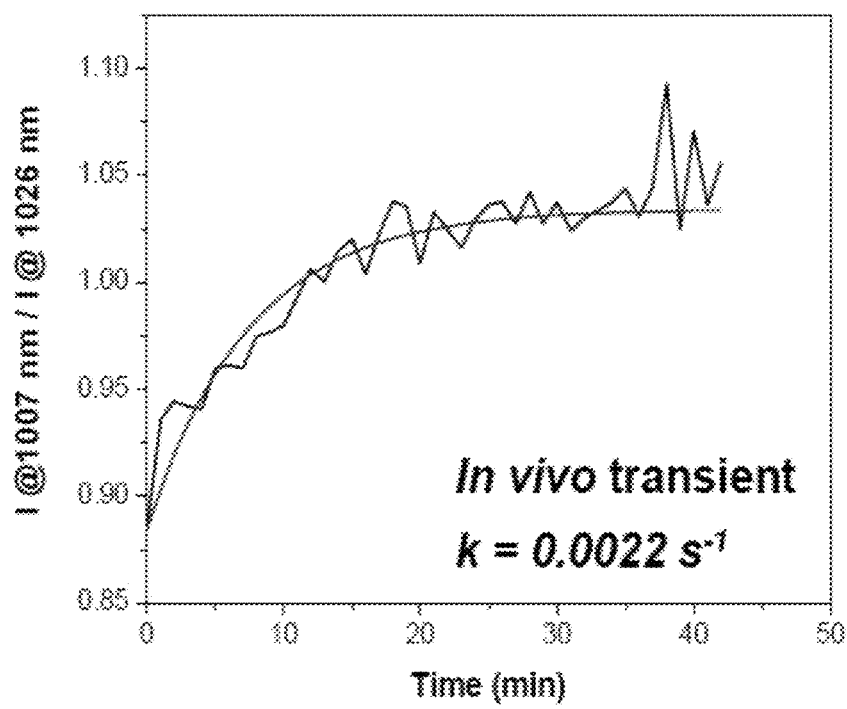
Figure 15B:
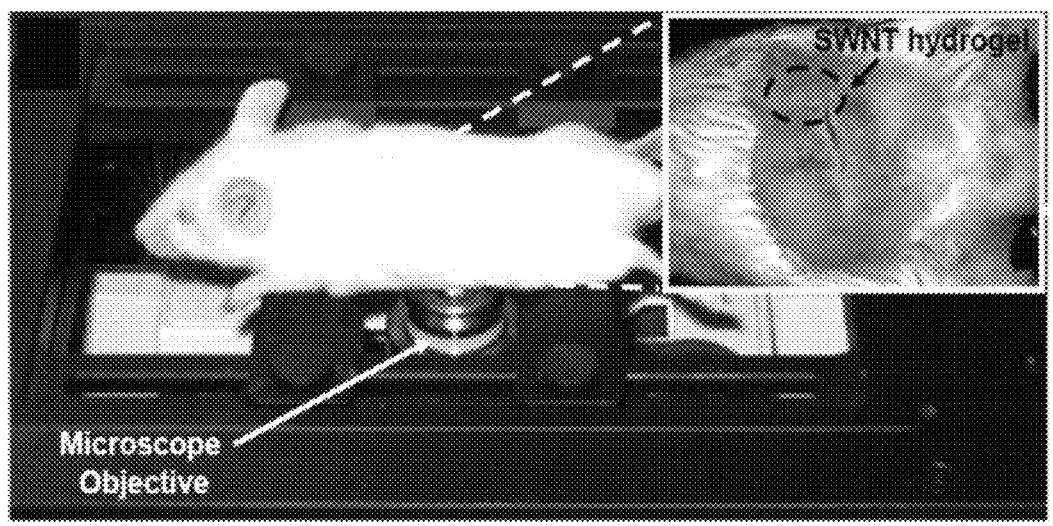

As previously mentioned, stimulus responsive hydrogels may be useful as sensors and drug delivery vehicles, one may envision a nanotube based sensor utilizing the mechanism outlined above coupled to such a hydrogel. FIG. 14A shows the transient response of a hydrogel with cross-linking $N_c^{-1}=0.003$ as the hydrogel was swollen and then dried. Both the swelling and deswelling were approximated as first-order processes, $\Delta E_{Norm}=\exp(-kt)$, with t being the time in seconds and k being the rate constant for the process. The measured PL shifts were normalized to fall between 0 and 1, The resulting modeled response is shown in FIG. 14A. Hydrogel swelling exhibited a $k=0.004$ s$^{-1}$. Hydrogel drying was almost an order of magnitude slower than swelling, and showed two distinct regions with time constants of $0.00062$ s$^{-1}$ and $0.00025$ s$^{-1}$. As a practical demonstration of measuring SWNT PL through tissue, a hydrogel was implanted subdermally in a mouse. The mouse was first euthanized through $CO_2$ asphyxiation. The mouse was shaved, a slit was cut in the abdominal skin with a scalpel, and the hydrogel was inserted between the dermis and the abdominal muscles. FIG. 14B shows SWNT PL from the same hydrogel outside of the mouse and implanted subdermally, respectively. The experimental set-up is shown in FIG. 15B, where the mouse was positioned over the microscope objective. From FIG. 14B, it is clear that with only visible excitation it is possible to detect SWNT PL through skin and tissue. FIG. 15A demonstrates transient swelling of a hydrogel, with $N_c^{-1}=0.003$, implanted subdermally (i.e. beneath the skin) in the mouse and swollen with water. The shift was presented as an intensity ratio of emission at 1007 nm, the peak center of the (6,5) nanotube in the wet hydrogel, and 1026 nm, the peak center in the dry hydrogel. As the emission maximum shifted, the reported ratio increased. Applying the same first order model as in FIG. 14A yielded a rate constant of $0.0022$ s$^{-1}$, the same order of magnitude as that determined for in vitro swelling. From FIG. 15A, a signal-to-noise ratio of 8.6 was calculated.

Figure 16:
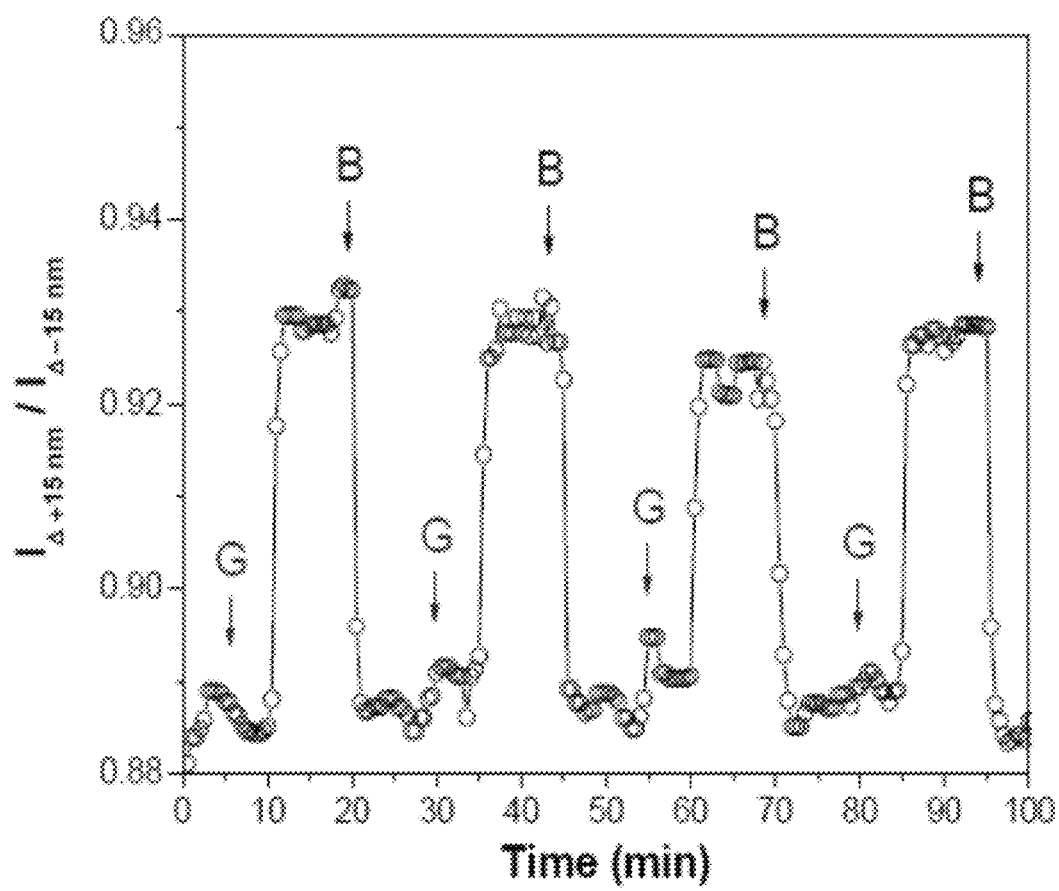

As a demonstration of the use of the hydrogel platform for sensing, a model glucose sensor was fabricated. Apo-glucose oxidase (ApoGOx), glucose oxidase without the cofactor, was chemically attached to the PVA hydrogel matrix for selective recognition of glucose. Upon periodical exposure to glucose, as shown in FIG. 16, the ApoGOx-attached hydrogel provided a reversible real-time change in signal. Since ApoGOx contains many lysine residual groups, it can act as a cross-linker to couple adjacent carboxylated PVA chains. Therefore, the ApoGOx-glucose interaction can cause changes in interior hydrostatic pressure and PVA chain conformation, resulting in a PL shift.

Materials

Single-walled carbon nanotubes were purchased from Southwest Nanotechnologies and subjected to the purification described below. Sodium cholate, sodium dodecyl sulfate, iodixonal, poly(vinyl alcohol) (85 kD to 124 kD Mw, 88% hydrolyzed) and glutaraldehyde were purchased from Sigma Aldrich and used as received.

Nanotube Suspension and Purification

Single-walled carbon nanotubes were first suspended in a 2 wt % sodium cholate (SC) aqueous solution using published methods. Nanotubes were mixed with a 2 wt % SC aqueous solution at a concentration of 1 mg/mL and probe tip sonicated, 6 mm tip, at 40% amplitude for 2 hrs in an ice bath. The solution was centrifuged 4 hrs at 30,000 RPM in a Beckman ultracentrifuge. The resulting nanotube solution was enriched in the (6,5) nanotube species using a modified density gradient procedure from the literature. Briefly, a SC-SWNT aqueous suspension was mixed with a 2 wt % sodium dodecyl sulfate (SDS) solution to a final ratio of 1:4 SDS:SC. Into a 16.8 mL Beckman ultracentrifuge tube was layered 3 mL 60% iodixanol, 6 mL of a 30% to 15% iodixanol step gradient and 4 mL of the SDS:SC suspended SWNT solution. All iodixanol layers contained 2 wt % surfactant in a ratio of 1:4 SDS:SC. The tubes were centrifuged 12 hrs at 32,000 RPM and 22° C. After centrifugation, the resulting gradient was fractionated into 250 µL fractions using a Beckman fractionator. Fractions were characterized by UV-vis-nIR absorption and fluorescence and fractions enriched in the (6,5) nanotube species from disparate tubes were combined.

Hydrogel Preparation

Iodixanol from the diameter purification procedure was first removed via dialysis, with enriched fractions being dialyzed against a 2 wt % SC solution. A 10 wt % PVA solution was prepared by dissolving the requisite amount of PVA in miliQ water at 80° C. The (6,5) enriched nanotubes were mixed with the 10% PVA in a 1:1 ratio to give a 5% PVA-SC-SWNT mixture. The PVA was assembled on the nanotube surface and the free SC was removed via dialysis. Hydrogels were then prepared by taking 1 mL of the PVA-SWNT solution adding glutaraldehyde, as the cross-linker, followed by 0.1M $H_2SO_4$, as the catalyst. The solution was poured into a Teflon mold and allowed to set overnight. After gelation, the hydrogels were rinsed with milliQ water until pH was constant and then dried under vacuum.

Measurement of SWNT Raman and Photoluminescence

Nanotube Raman scattering was collected with a Kaiser Raman RXN system with a 785 nm laser photodiode. Nanotube photoluminescence from the hydrogels was measured using a home built near infrared PL microscope. Briefly, a Zeiss AxioVision inverted microscope was coupled to a Princeton Instruments InGaAs 1-D array detector through a PI-Acton SP150 spectrograph. A white light excitation source coupled to a monochromator was used for excitation light.

Measurement of SWNT PL In Vivo

A male mouse was first asphyxiated using $CO_2$. The mouse was then shaved to remove excess fur and a small slit was cut into the skin, being careful not to puncture the peritoneum. The hydrogel was inserted into the slit and the mouse was placed belly side down on a glass cover slip. Nanotube spectra were taken with the same apparatus as described above.

The Effect of Nanotube Loading

To test the effect of nanotube loading on the SWNT PL response in the hydrogel, the starting PVA-SWNT solution was diluted with 10 wt % PVA and water so as to maintain the PVA concentration in the sample. As a measure of nanotube loading, the area under the SWNT optical transitions was calculated after background subtraction. The hydrogels were formed as described previously and spectra in the dry and wet state were taken. FIGS. 17A and 17B show plots demonstrating the nanotube fluorescence shift from the dry to the wet hydrogel versus nanotube loading. There was no change in the observed shift with nanotube loading and thus exciton energy transfer can be discounted as a mechanism for the observed shifts The Effect of SWNT Length To determine if nanotube length was playing a role in the observed optical shifts, the nanotubes were first length sorted before suspending them in PVA. The length sorting was accomplished using dynamic density gradient centrifugation. Briefly, nanotubes were suspended in sodium deoxycholate using a similar method as that described above. The resulting nanotube suspension was mixed with iodixonal to give a 22.5 wt % iodixonal layer. To a 38.8 mL centrifuge tube was layered 6 mL 60% iodixonal, 3 mL SWNT and 15 mL 18% iodixonal. All layers contained 2 wt % sodium deoxycholate. The solution was centrifuged 71 hr at 13,800 RPM. After centrifugation the samples were fractionated into 1 ml, fractions and their lengths were analyzed. Three different lengths were chosen for analysis and were used in the synthesis of PVA hydrogels as described above. FIG. 18 shows the shift in energy from the wet to dry hydrogel for the (6,5) nanotube versus nanotube length. Changing the nanotube length did not appear to cause the observed shift to change.

Fitting the SWNT PL Shifts

The observed SWNT PL shifts in the hydrogel were fitted using the model discussed above. The fits for the 12 data sets are shown in FIGS. 19-20, with FIG. 19 including the fits for the wet hydrogel data and FIG. 20 including the fits for the dry hydrogel data.

Glucose-Sensitive Hydrogel

Figure 22:
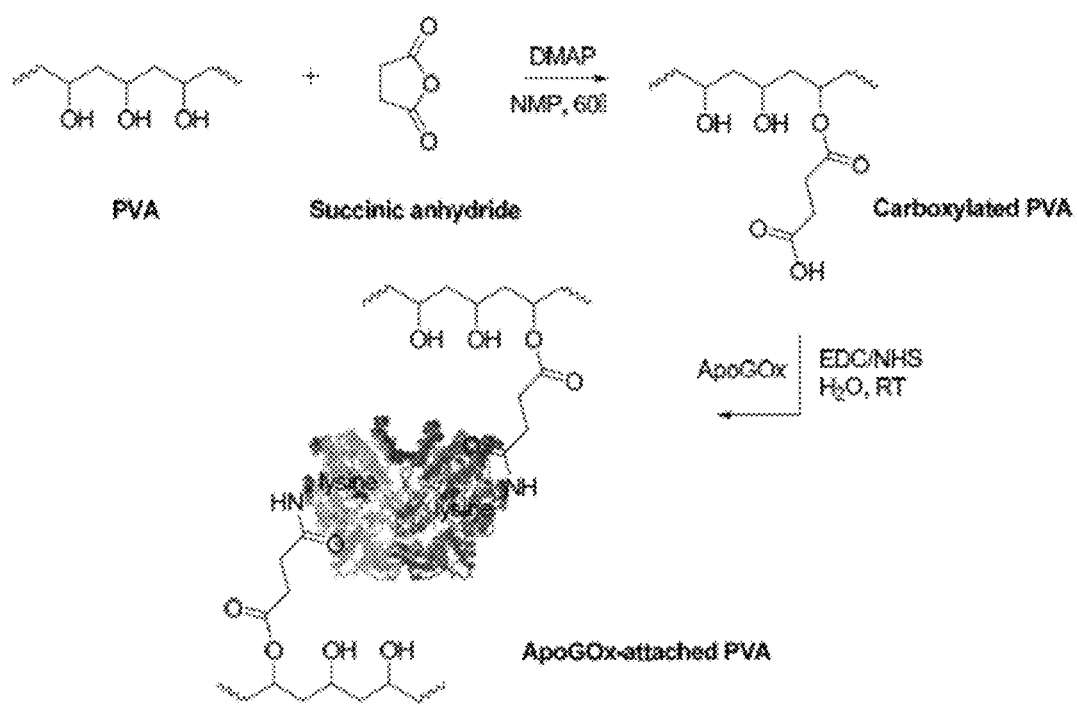
FIG. 22 includes a schematic illustration of the reaction steps for the covalent attachment of ApoGOx to PVA-SWNT hydrogel, according to one set of embodiments.

Hydrogel Preparation: First, 1 mL of PVA-SWNT solution was cross-linked with 7 µL glutaraldehyde and 5 µL 0.1M $H_2SO_4$ to give a hydrogel ($N_c^{-1}$=0.07). The PVA/SWNT hydrogel was reacted with succinic anhydride (0.12 mmol) and 4-(dimethylamino)pyridine (DMAP) (0.12 mmol) in N-methyl-2-pyrrolidone (NMP) for the carboxylation of PVA (at a —COOH/—OH molar ratio of 1/10). The reaction proceeded over 24 hours at 60° C. The resulting hydrogel sample was thoroughly washed with excess distilled water. To covalently attach apo-glucose oxidase (ApoGOx) to the PVA hydrogel matrix, the carboxylated PVA-SWNT hydrogel was activated with N-(3-dimethylaminopropyl)-N'-ethylcarbodiimide hydrochloride (EDC)/N-hydroxysuccinimide (NHS) (1.1 mmol/1.1 mmol) in distilled water and subsequently mixed with 0.5 mL of ApoGOx solution (6.3 µg mL−1). The overall procedure is illustrated schematically in FIG. 22.

Figure 23:
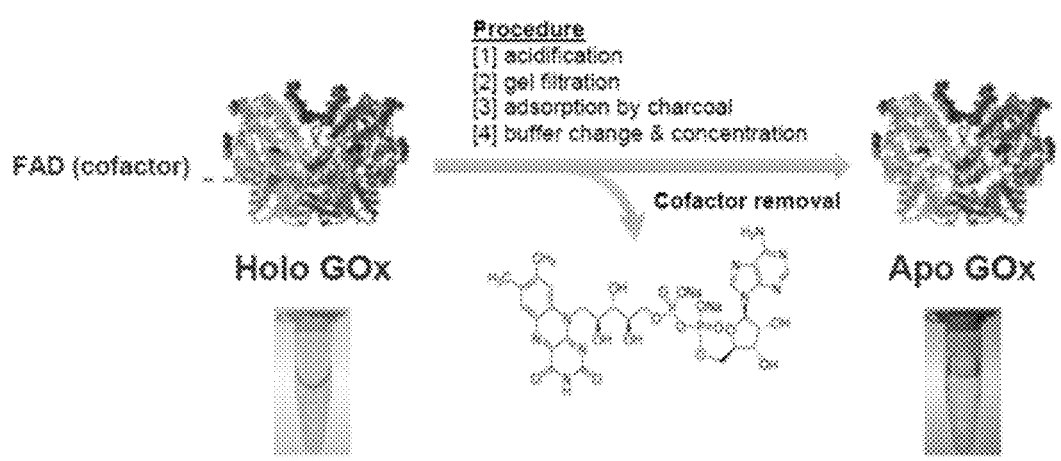
FIG. 23 includes a schematic illustration of the preparation of ApoGOx from holo-glucose oxidase, according to one set of embodiments.
Figure 24:
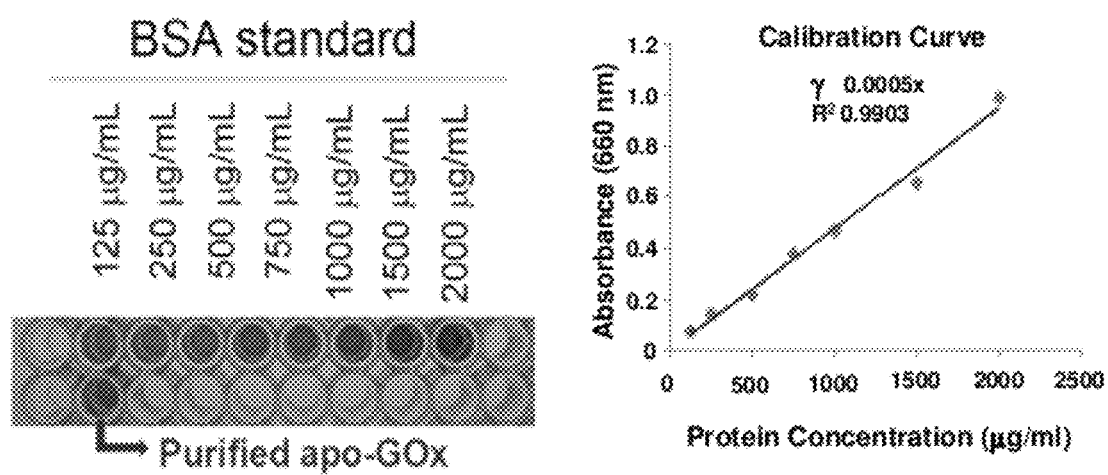
FIG. 24 outlines a Bradford assay for determining the concentration of as-obtained ApoGOx, according to one set of embodiments.
Figure 25:
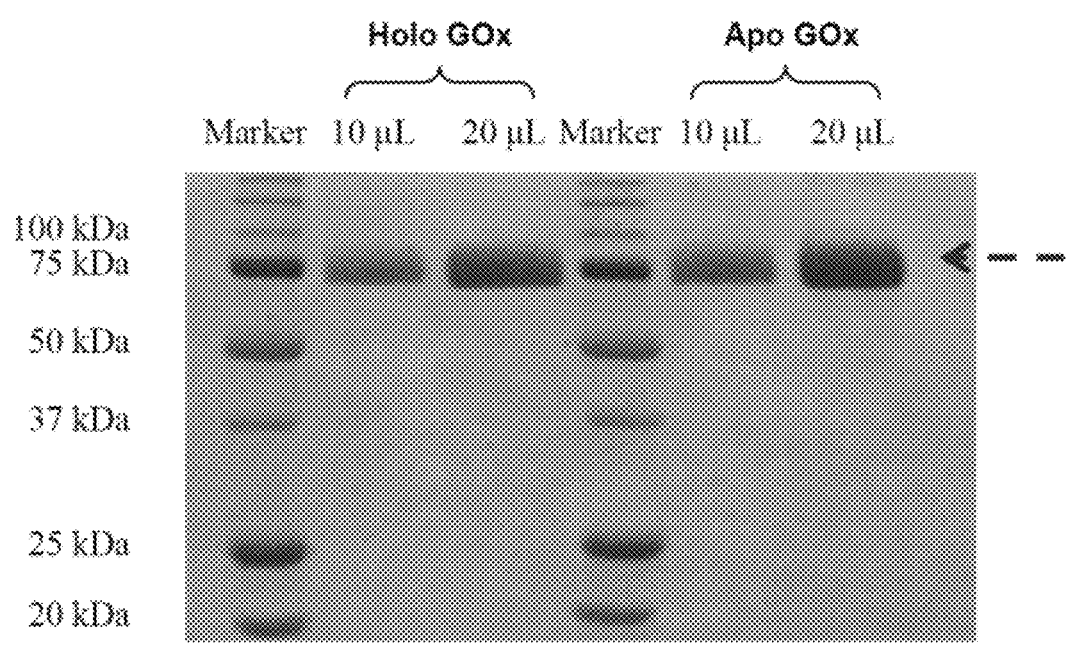
FIG. 25 outlines a SDS-PAGE analysis of ApoGOx prepared from HoloGOx, according to one set of embodiments.

ApoGOx Preparation: FIG. 23 depicts the preparation of ApoGOx from holo-glucose oxidase by removing the FAD cofactor. GOx (100 mg) was dissolved in 30% (w/v) glycerol in 25 mM sodium phosphate buffer, pH 6.0. The GOx solution was stirred on ice bath and acidified to pH 1.7 by addition of ice cold 30% (w/v) glycerol in 25 mM phosphate-H2SO4, pH 1.1. This mixture was incubated for 30 min at 0° C. and loaded on a Sephadex G-25 column (GE heathcare) equilibrated with 30% (w/v) glycerol 25 mM sodium phosphate buffer, pH 1.7. The eluted fractions were spectrophotometrically analyzed ($\lambda$=280 nm), and the samples containing the protein were collected directly into a dextran-coated charcoal solution suspended in 400 mM sodium phosphate, pH 8.0. The pH of charcoal mixture was adjusted to pH 6.8 with 1 N NaOH and the solution and stirred for 30 min at ice bath. The resulting solution was centrifuged and filtered with 0.45 µm syringe filter. The resulting solution was centrifuged through a centrifugal filter with molecular weight cutoff of 100 kDa (Millipore) trice to exchange buffer with 10 mM sodium phosphate buffer, pH 6.8. The concentration of prepared ApoGOx was determined to be 6.3 µg mL$^{-1}$ by Bradford assay (FIG. 24) and protein size was confirmed by 12% SDS-PAGE as indicated by the arrow in FIG. 25.

Figure 26:
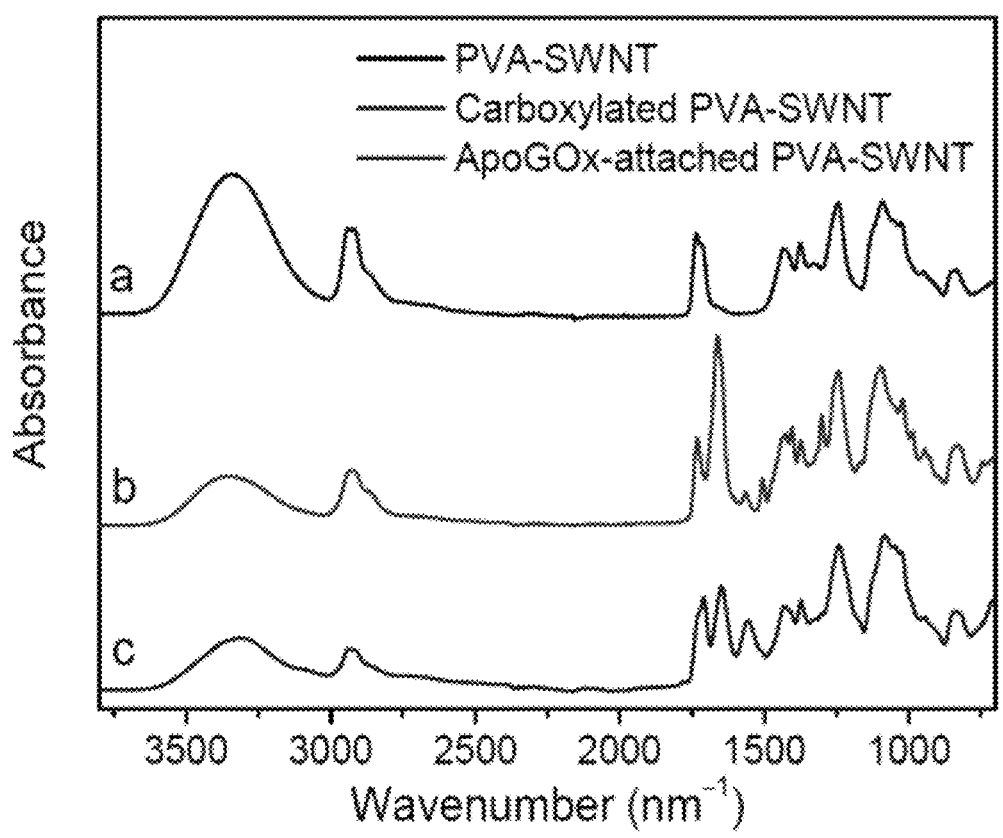
FIG. 26 includes ATR-IR spectra of (a) PVA-SWNT, (b) carboxylated PVA-SWNT, and (c) ApoGOx-attached PVA-SWNT hydrogels, according to one set of embodiments.

Characterization of the Hydrogel: Chemical characterization of the samples was carried out using attenuated total reflection-infrared (ATR-IR) spectroscopy (FIG. 26). First, ATR-IR spectrum of PVA/SWNT hydrogel showed characteristic peaks at 3300, 2930, and 1725 cm$^{-1}$, which were assigned to hydroxyl groups, alphatic hydrocarbons, and residual acetate groups. The carboxylated PVA-SWNT hydrogel displayed a new carboxylic acid stretching peak at 1670 cm$^{-1}$. After ApoGOx attachment, the absorption peak originating from amide I (at 1640 cm$^{-1}$) was to indistinguishable in the spectrum due to the peak superposition. Instead, the 1550 cm$^{-1}$ peak from amide II could be observed. These results support the covalent attachment of ApoGOx to the PVA-SWNT matrix.

Figure 27A:
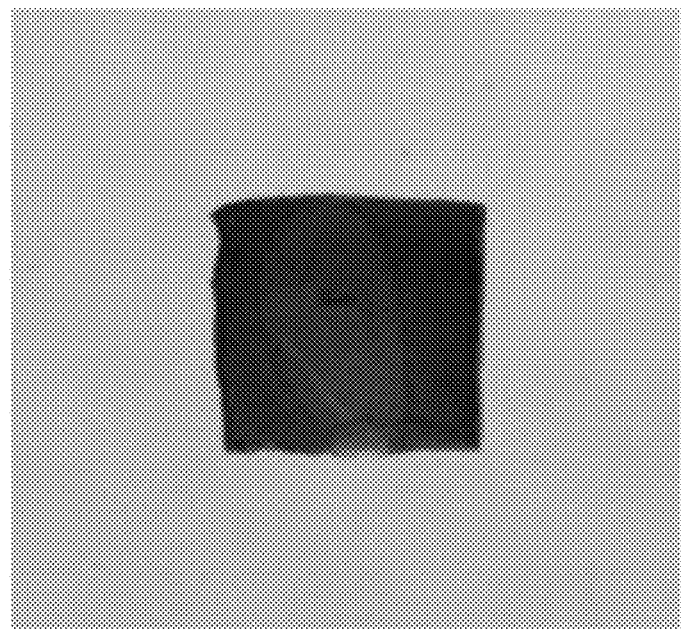
FIG. 27 includes photographs of commassie-dye stained hydrogels for (27A) a ApoGOx-attached PVA-SWNT hydrogel and (27B) a PVA-SWNT hydrogel (control), according to one set of embodiments.
Figure 27B:
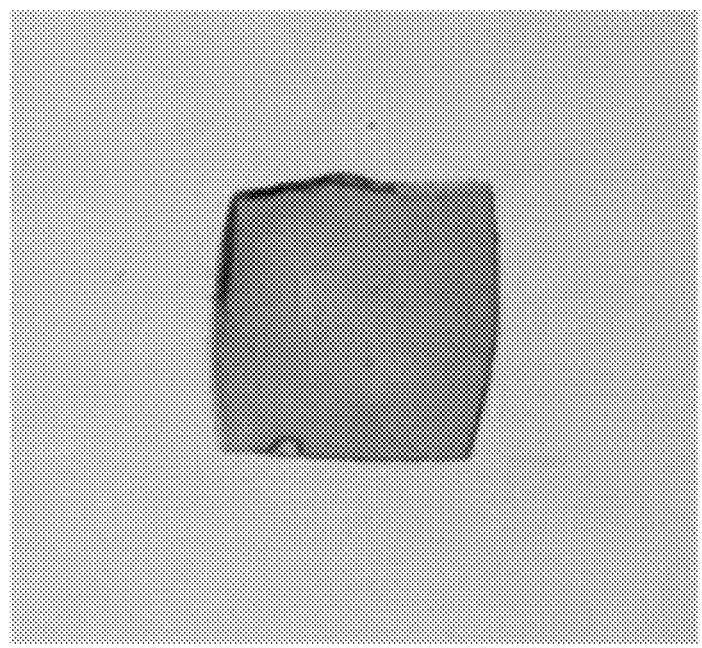

In addition, the hydrogel was stained by Coomassie dye to further confirm the incorporation of ApoGOx. The dye was bound selectively to proteins via physiorption to arginine, aromatic amino acids, histidine, and so forth. As shown in FIGS. 27A and 27B, the ApoGOx-attached hydrogel appeared blue in color while PVA-SWNT control hydrogel had little color change. Judging from this result, it was evident that the ApoGOx was incorporated into the hydrogel. The hydrogels were stained for 1 h with Coomassie Brilliant Blue R-250 and decolored with destaining solution.

Figure 28:
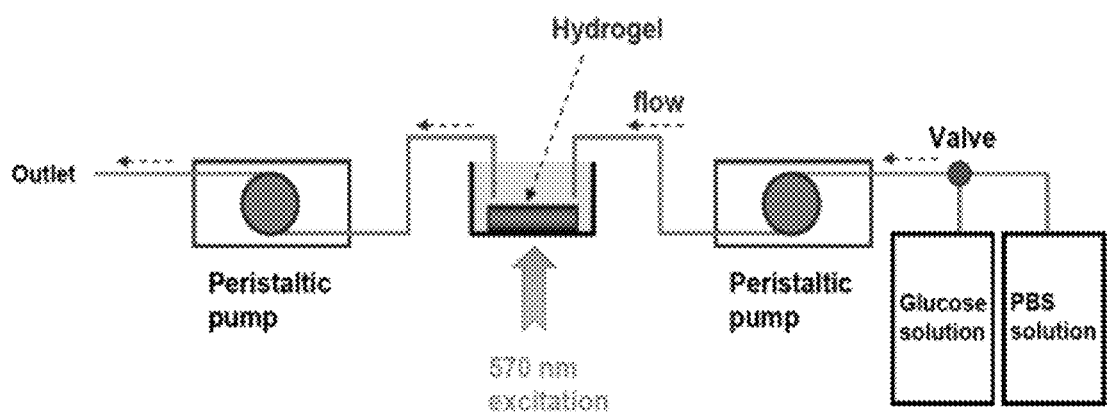
FIG. 28 includes a schematic diagram of the experimental setup for reversible glucose detection, according to one set of embodiments.
Figure 29:
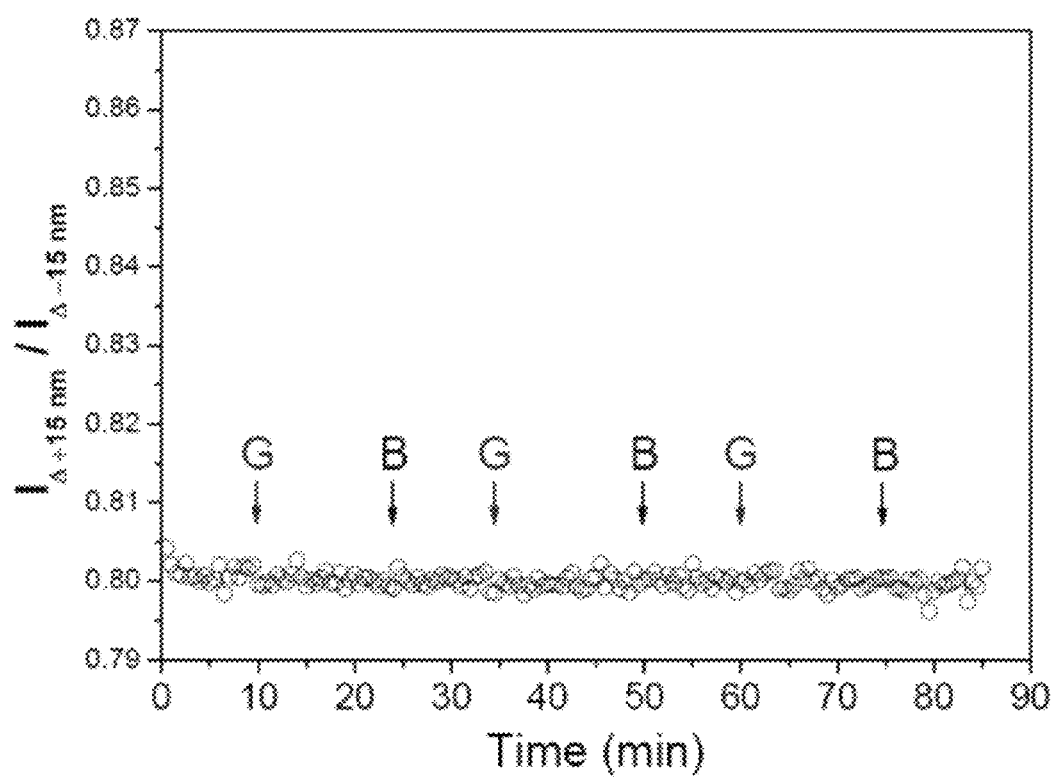
FIG. 29 is a plot of responses of a PVA-SWNT hydrogel with no ApoGOx attached (G: 10 mM glucose; B: PBS solution), according to one set of embodiments.

Experimental Set-up for Reversible Detection: FIG. 28 represents an experimental set-up for measuring the optical response of hydrogels in real time. The flow rate was 120 mL min$^{-1}$. In the control experiment, the PVA-SWNT hydrogel with no ApoGOx attached showed no remarkable responses to glucose, as illustrated in FIG. 29.

Glucose Sensitive Hydrogel Microparticles

Hydrogel microparticles with embedded single-walled carbon nanotubes (SWNT) were synthesized by free radical precipitation polymerization. (Zhang, Y., et al., Biomacromol. 2006, 7, 3196-3201, incorporated by reference in its entirety). SWNT were first dispersed in sodium dodecyl sulfate (SDS), using established procedures. (O'Connell, M. J., et al.; Science 2002, 297, 593-596, incorporated by reference in its entirety). The SDS-SWNT suspensions were then diluted in NanoPure $H_2O$, giving a final SDS concentration of 6.9 mM. Acrylic monomers, 0.138 M, were dissolved in the SDS-SWNT solution and heated to 70° C. under a $N_2$ blanket. Monomers used for gelation included a combination of the following; acrylamide, hydroxyethyl methacrylate and N-isopropylacrylamide. Methacrylic acid was always included to provide carboxylic acid groups for further hydrogel modification. Either 2-hydroxy-3-phenoxypropyl acrylate or hexyl acrylate were used as hydrophobic groups for non-covalent attachment to SWNT. Cross-linking, using N,N'-methylenebis-(acrylamide), was initiated with ammonium persulfate and allowed to continue for 6 hrs. The resulting hydrogels had hydrodynamic radii ($R_h$) on the order of hundreds of nanometers and were found to be sensitive to pH due to the encorporated carboxylic acids.

Figure 30A:
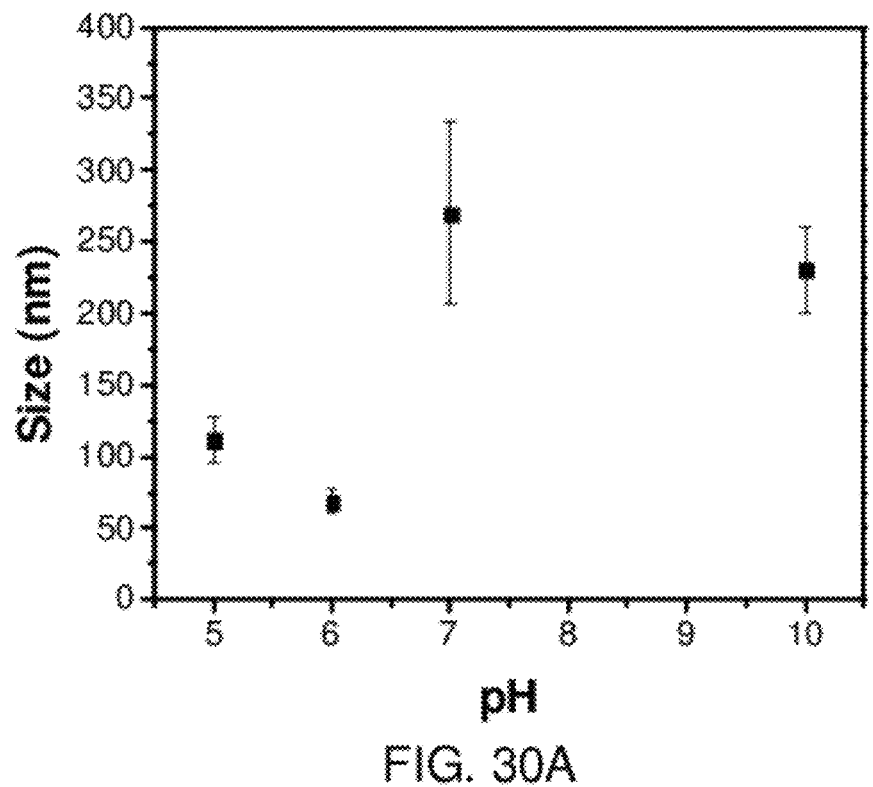
FIG. 30 is a plot of the (30A) hydrodynamic radius of poly(hydroxyethyl methacrylate-co-methacrylic acid) microgels with SWNT embedded as the solution pH is changed from 5 to 10 and (30B) the photoluminescence intensity of SWNT embedded in the microgels at pH 5 and pH 7, when the microgel has swollen 2.5×.
Figure 30B:
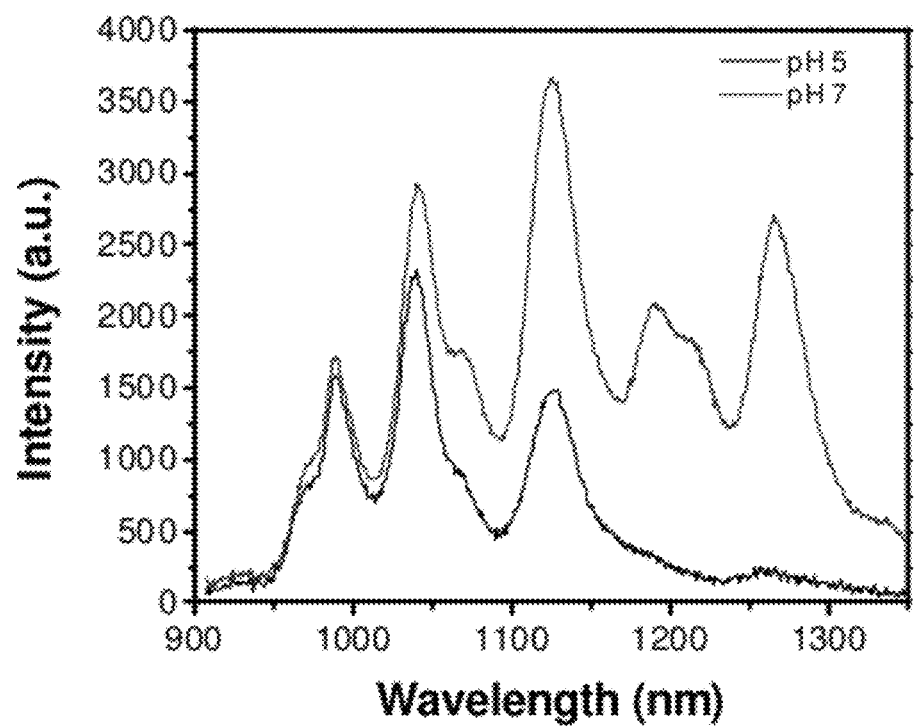

As a proof of concept demonstrating SWNT photoluminescence (PL) modulation in response to hydrogel swelling, microgel particles were exposed to solutions having pH values from 5 to 10. The microparticles swelled from $R_h$=75 nm to 250 nm (FIG. 30A). As the hydrogel particles were swollen, the SWNT PL is also modulated. FIG. 30B shows large diameter (smaller bandgap) nanotube PL was quenched when the hydrogels were contracted and increased with hydrogel swelling.

This sensing mechanism was easily extended to a glucose responsive hydrogel by modifying the particles with 3-aminophenylboronic acid via carboxyl groups contained in the hydrogel. Phenylboronic acids have previously been demonstrated to bind to glucose, shifting the $pK_a$ of the boronic acid. Upon glucose binding the boronic acid gained a net negative charge, inducing the hydrogel to swell.

Glucose Detection in Chloroplasts

Figure 31A:
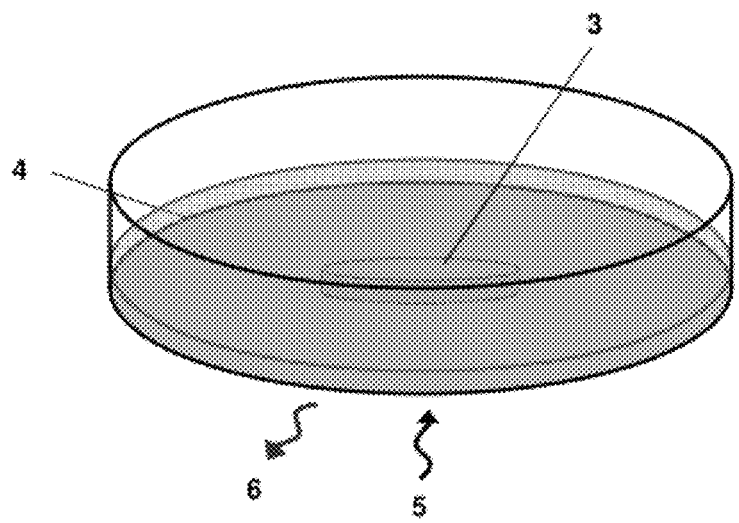
FIG. 31A is a schematic of the collagen-SWNT based platform for single-molecule glucose detection.
Figure 31B:
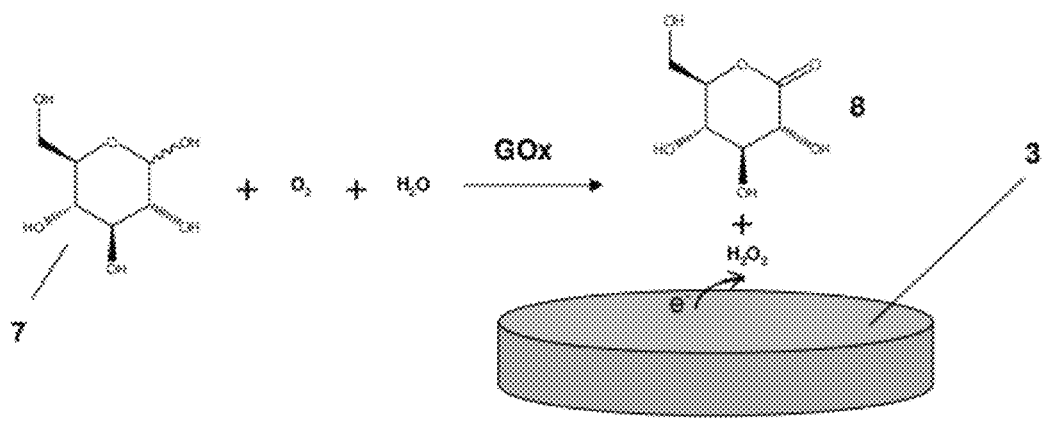
FIG. 31B illustrates a buffered solution containing glucose oxidase placed atop the collagen-SWNT film and converting glucose to hydrogen peroxide, which quenches individual SWNT fluorescence.
Figure 32A:
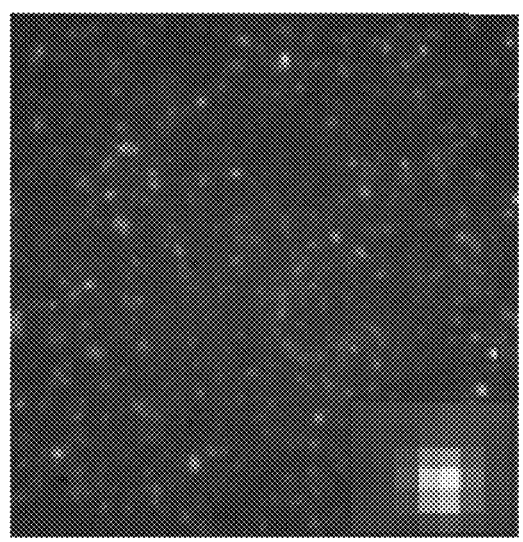
FIG. 32A. is an nIR fluorescence image.
Figure 32B:
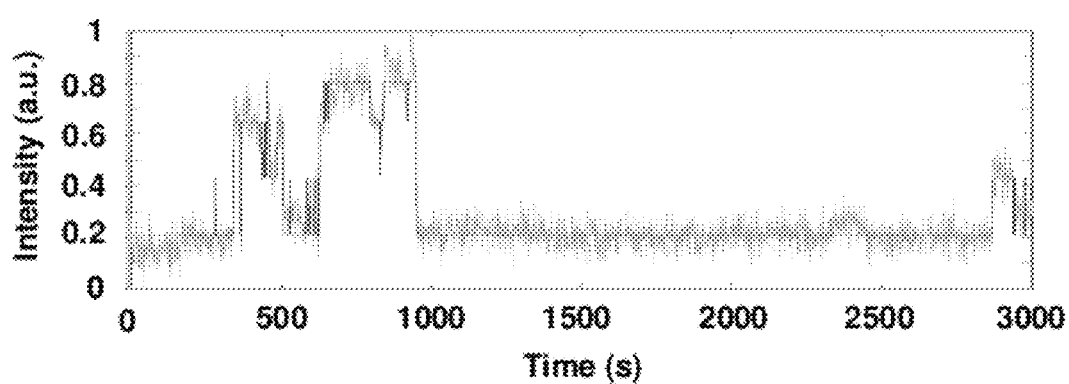
FIG. 32B is fluorescence trace of individual SWNT after glucose addition.

Collagen-embedded SWNT films (3) were synthesized and placed in a buffered solution containing glucose oxidase (4, FIGS. 31A and 31B). Under 785 nm excitation (5), the SWNT fluorescence, in the near-infrared, was imaged on an InGaAs array detector (6). Upon β-D-glucose (7) addition, glucose oxidase (GOx) catalyzed the conversion of 7, oxygen and water to D-glucono-1,5-lactone (8) and hydrogen peroxide. The binding of hydrogen peroxide molecules to 3 resulted in the reversible single-molecule quenching of SWNT fluorescence (FIGS. 31B and 32A). The repeated binding and release of these peroxide molecule resulted in the quenching and unquenching of SWNT fluorescence. The resulting traces of the fluorescence intensity of a single nanotube (FIG. 32B) exhibited "steps", which were indicative of single-molecule binding and un-binding.

Figure 33A:
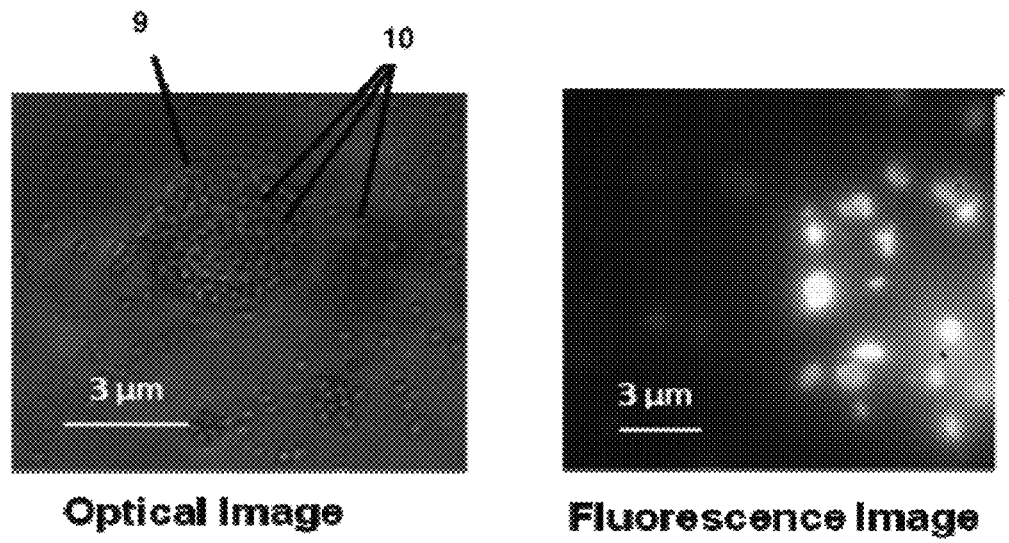
FIG. 33 includes (FIG. 33A) optical (left) and fluorescence (right) verification of chloroplast isolation and (FIG. 33B) confirmation of chloroplast photoactivity.
Figure 33B:
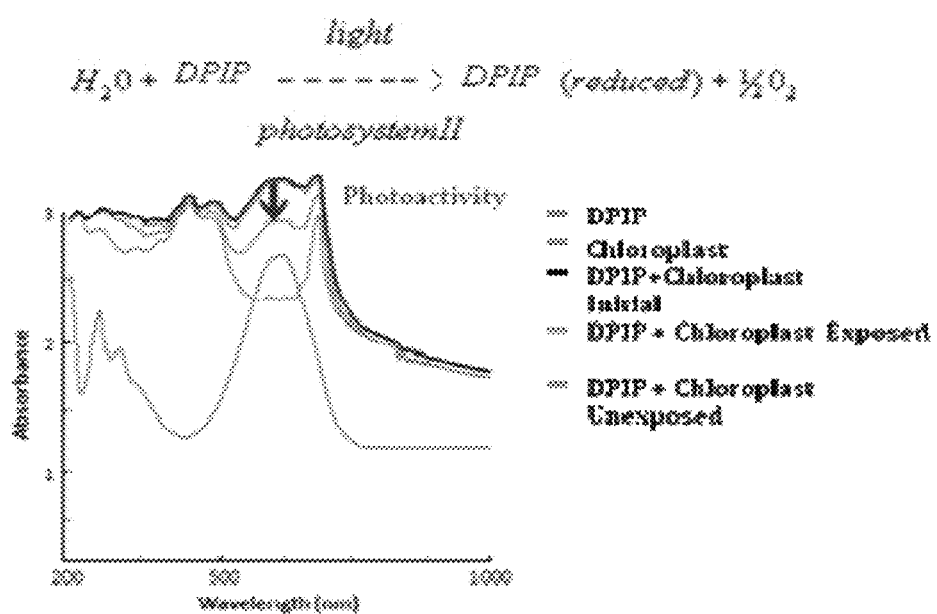
Figure 34A:
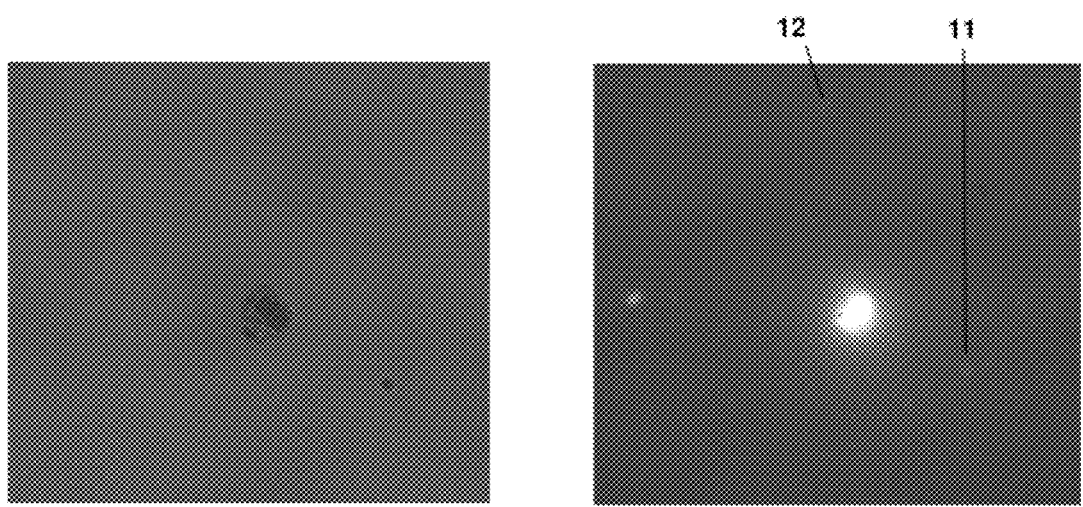
FIG. 34 includes (FIG. 34A) images of chloroplasts (left) placed on the collagen-SWNT film (right). SWNT fluorescence was monitored under illumination at 785 nm.
FIG. 34B is a plot of the fluorescence trace of the radiation emitted in the vicinity of the chloroplast, indicating glucose emissions from individual chloroplasts.
FIG. 34C shows fluorescence traces farther from the chloroplasts.
Figure 34B:
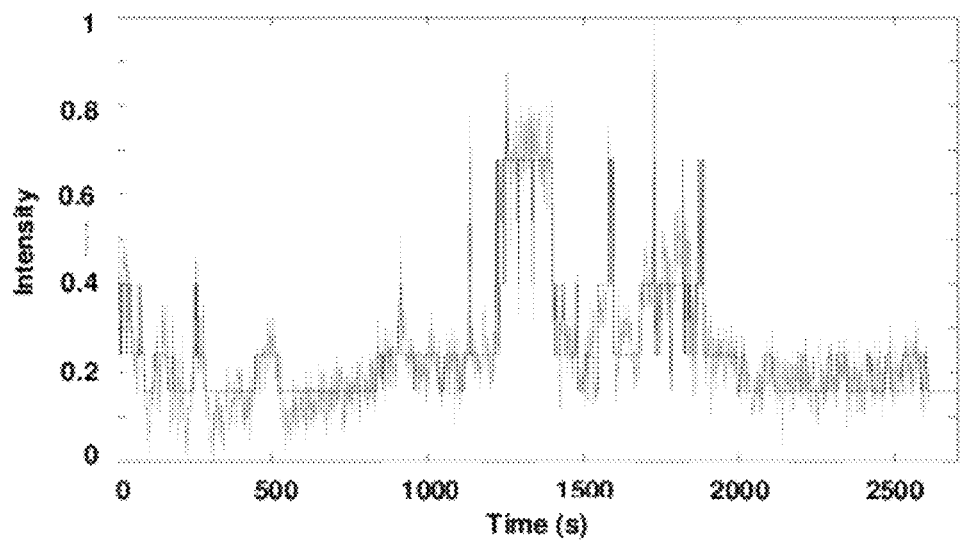
Figure 34C:
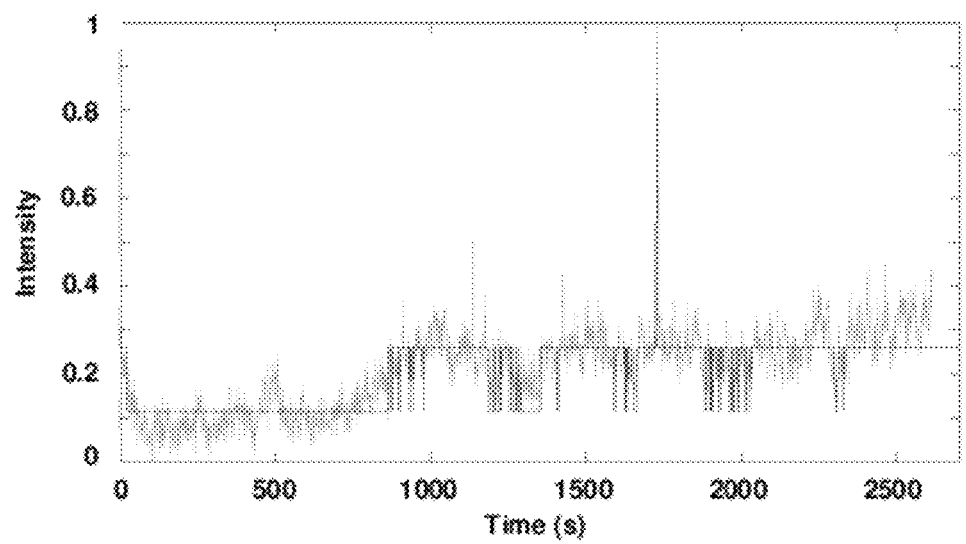

To apply this platform for measuring individual chloroplast glucose emissions, chloroplasts (9) were first isolated according to literature via mechanical abrasion and centrifugation (FIG. 33A). (Giebel, P. E.; 1980; Association for Biology Laboratory Education; Tested Studies for Laboratory Teaching Vol. 2, Chap. 3, incorporated by reference in its entirety). Chloroplast isolation was confirmed using optical and fluorescence images, and photoactivity was established via photoabsorption in the presence of a dye indicator (FIGS. 33A and 33B). At dilute concentrations, single chloroplasts were placed atop 3, as shown in FIG. 34A. Individual SWNT fluorescence traces were monitored for 7 in the vicinity (11) and far (12) from the chloroplast. SWNT traces in the vicinity of the chloroplast exhibited step-like behavior (FIG. 34B), whereas traces further from the chloroplast were relatively flat (FIG. 34C). This observance was characteristic of glucose detection from chloroplast emissions.

Glucose Binding Protein Modified PVA/SWNT for Glucose Detection

Glucose binding protein (GBP, 1) is a globular periplasmic protein capable of binding glucose with micromolar affinity. (D'Auria, et al., Biotechnol. Prog. 2004, 20, 330-337). This protein has a monomeric structure that folds in two main domains linked by three strands commonly referred to as the 'hinge', and the glucose-binding site is included in the cleft between the two lobes of the bilobate protein. (Borrok, M. J., et al. Protein Sci. 2007, 16, 1032-1041; Careaga, C. L., et al. Biochemistry 1995, 34, 3048-3055.) Importantly, GBP undergoes a large conformational change by hinge bending upon glucose binding, making it ideal as a biological-recognition element for the development of glucose biosensor.

GBP was conjugated with polyvinyl alcohol (PVA)-wrapped SWNT (2) to induce an optical signal change for direct glucose detection. The conformational change of GBP on the SWNT surface resulted in quenching of SWNT fluorescence, and the fluorescence quenching was correlated quantitatively to the concentration of glucose.

Figure 35A:
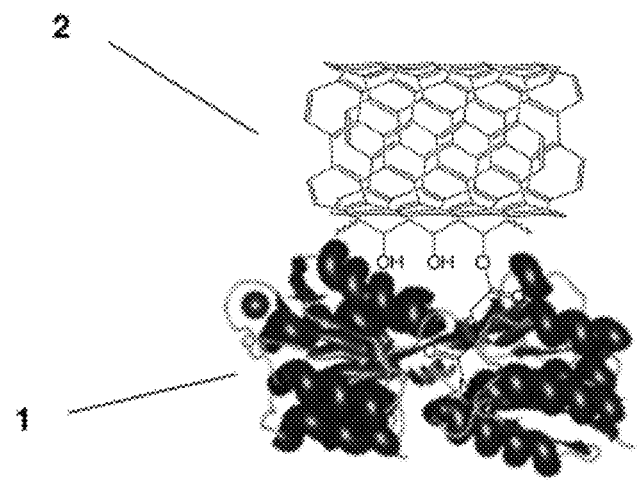
FIG. 35A is a schematic of GBP-PVA/SWNT.
Figure 35B:
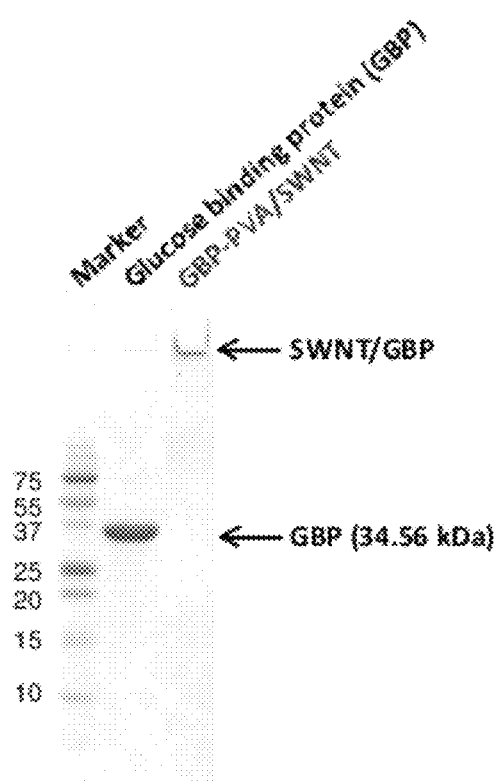
FIG. 35B shows an SDS-PAGE image for GBP-PVA/SWNT and only GBP demonstrating successful GBP attachment.

FIG. 35A schematically illustrates the structure of GBP-PVA/SWNT. SWNTs were functionalized with carboxylated PVA and then GBP was covalently attached to the polymer via a condensation reaction. The attachment of GBP to SWNT was confirmed by SDS-PAGE analysis, as shown in FIG. 35B. There was no free GBP in the sample.

Figure 36A:
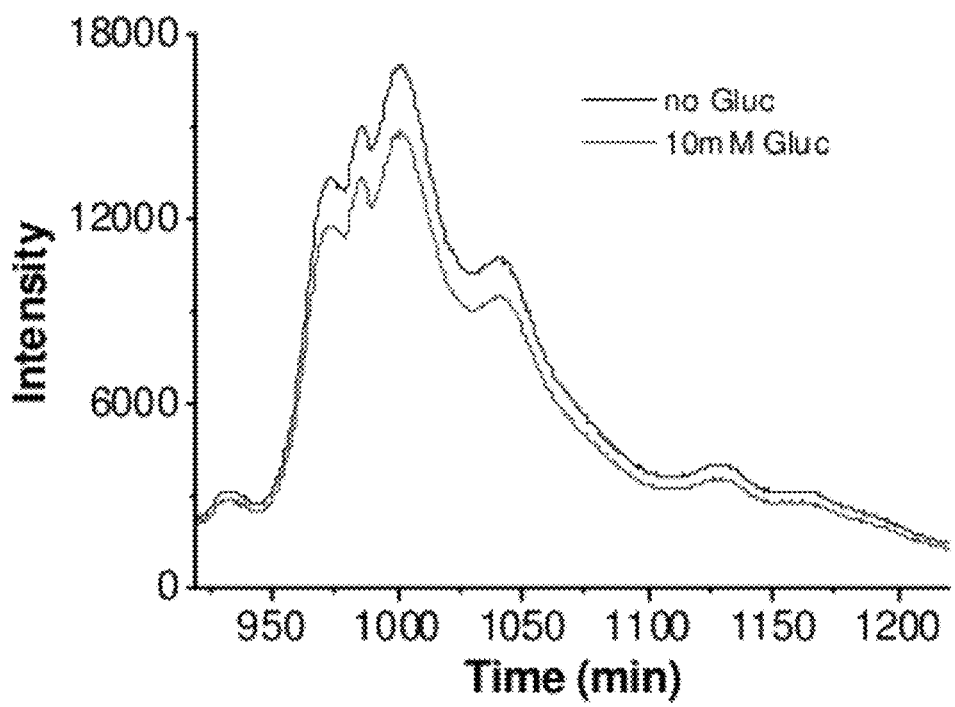
FIG. 36A shows fluorescence peaks of GBP-PVA/SWNT before and after 10 mM glucose addition.
Figure 36B:
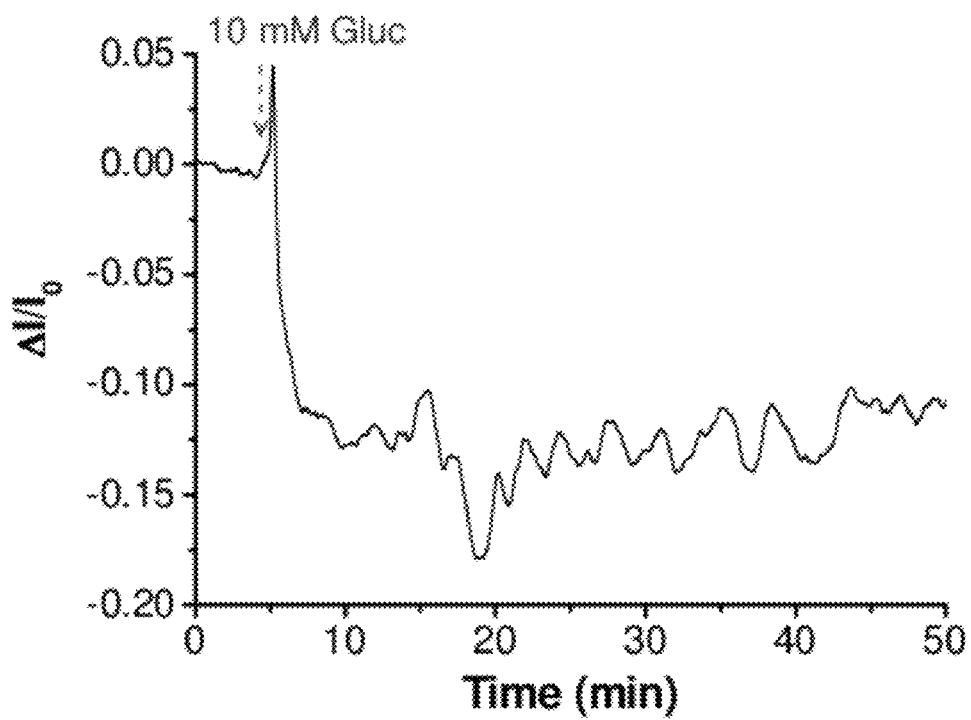
FIG. 36B is a plot of the real-time response upon 10 mM glucose addition: the normalized intensity change, $\Delta I/I_0 = (I-I_0)/I_0$ is plotted, where I is the real-time intensity and $I_0$ is the initial intensity.
Figure 37A:
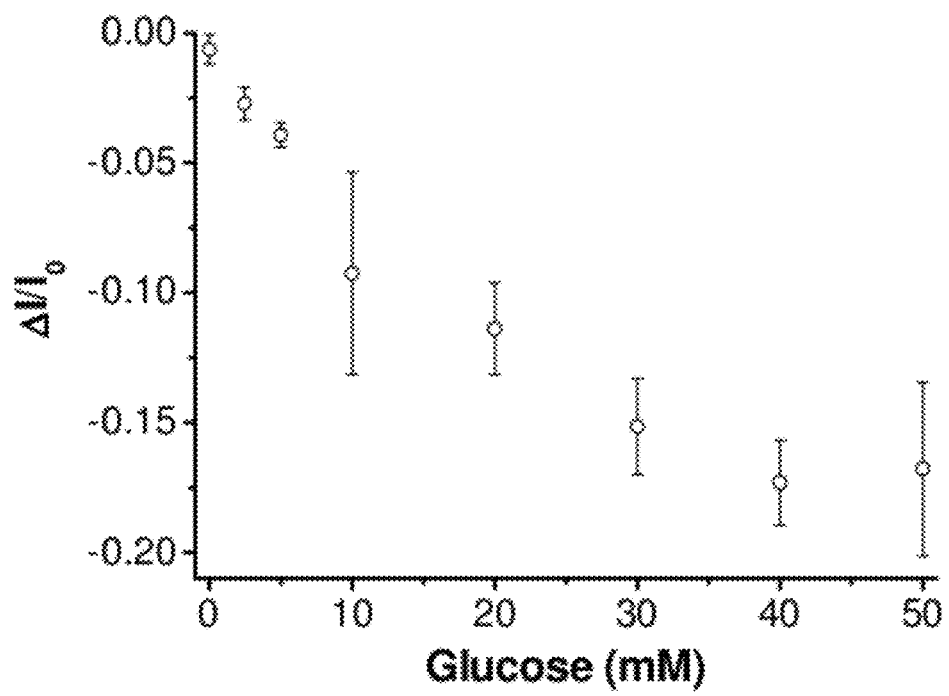
FIG. 37A is the calibration curve of GBP-PVA/SWNT.
Figure 37B:
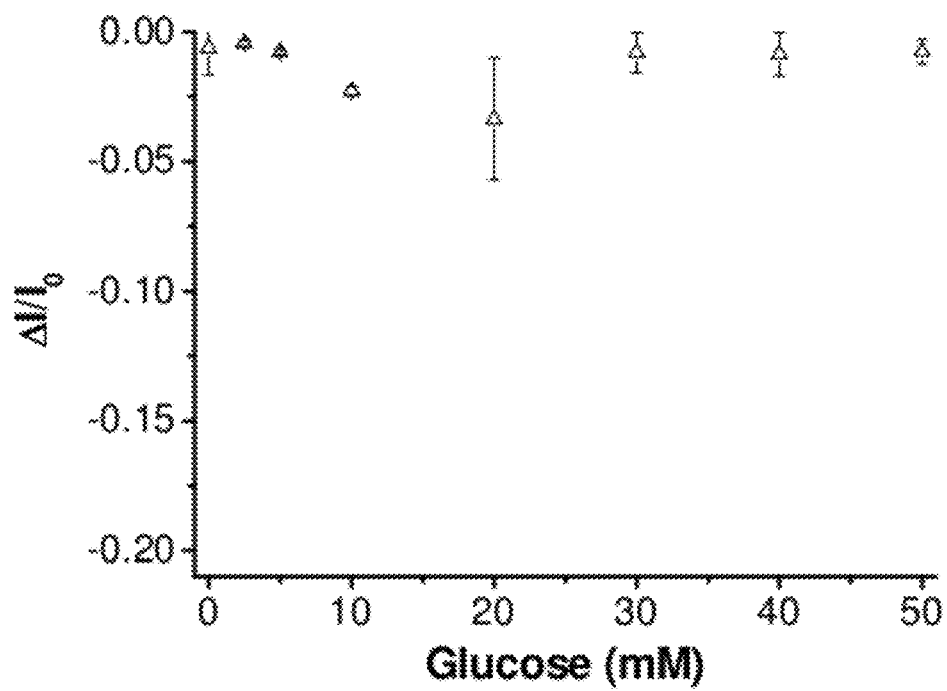
FIG. 37B shows the calibration curve of PVA/SWNT with no GBP attached: the sensitivity was determined from the saturated I/I0 value.
Figure 38:
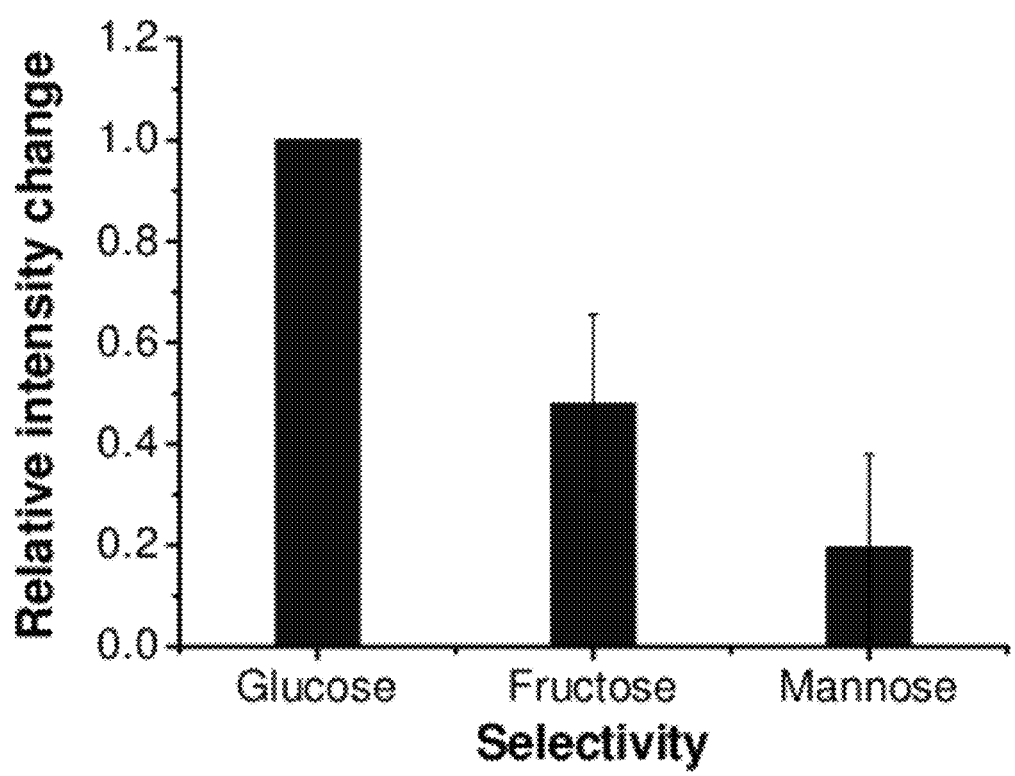
FIG. 38 is a histogram showing the selectivity of GBP-PVA/SWNT.

Upon addition of glucose, GBP-PVA/SWNT showed a decrease in fluorescence (FIG. 36A). When the fluorescence was measured in real-time, it rapidly decreased before finally leveling off (FIG. 36B). The calibration curve presented linear behavior at low concentrations, but nonlinear behavior was observed at concentrations of more than 40 mM (FIG. 37A). A control experiment was performed using PVA/SWNT with no GBP attached (FIG. 37B). In this case, there was little response over a wide range of glucose concentrations. Lastly, GBP-PVA/SWNT showed high selectivity toward glucose, as shown in FIG. 38.

A number of embodiments of the invention have been described. Nevertheless, it will be understood that various modifications may be made without departing from the spirit and scope of the invention. It should also be understood that the appended drawings are not necessarily to scale, presenting a somewhat simplified representation of various preferred features illustrative of the basic principles of the invention.

What is claimed is:

1. A method for determination of an analyte, comprising:
   exposing a composition comprising a stimulus-responsive hydrogel and a photoluminescent nanostructure embedded in the stimulus-responsive hydrogel to a sample suspected of containing an analyte, wherein the analyte, if present, interacts with the composition to alter a structure of the stimulus-responsive hydrogel, causing a change in photoluminescence emission of the photoluminescent nanostructure; and
   determining the change in photoluminescence emission of the photoluminescent nanostructure, thereby determining the analyte.

2. The method of claim 1, wherein the photoluminescent nanostructure comprises a single-walled carbon nanotube.

3. The method of claim 1, wherein the hydrogel is responsive to a stimulus comprising exposure to an analyte.

4. The method of claim 3, wherein the analyte comprises glucose.

5. The method of claim 3, wherein the analyte comprises an antibody.

6. The method of claim 3, wherein the analyte comprises an antigen.

7. The method of claim 1, wherein the stimulus comprises a change in temperature.

8. The method of claim 1, wherein the stimulus comprises a change in pH.

9. The method of claim 1, wherein the change in the photoluminescence comprises a change in photoluminescence intensity, a change in peak wavelength, a Raman shift, or a combination thereof.

10. The method of claim 1, wherein altering a structure of the composition comprises altering the amount of cross-linking in the hydrogel.

11. The method of claim 1, wherein altering a structure of the composition comprises altering the volume of the composition.

12. A composition, comprising:
   a stimulus-responsive hydrogel, and a photoluminescent nanostructure embedded in the stimulus-responsive hydrogel, wherein the photoluminescence emission of the photoluminescent nanostructure is effected by a change in a characteristic of the stimulus-responsive hydrogel.

13. The composition of claim 12, wherein the photoluminescent nanostructure comprises single-walled carbon nanotubes.

14. The composition of claim 12, wherein the photoluminescent nanostructure comprises semi-conductor quantum dots.

15. The composition of claim 12, wherein the photoluminescent nanostructure comprises semi-conductor nanowires.

16. The composition of claim 12, wherein the photoluminescent nanostructure comprises graphene.

17. The composition of claim 12, wherein the hydrogel comprises poly(vinyl alcohol).

18. A method, comprising:
    providing a composition comprising a stimulus-responsive hydrogel, and a photoluminescent nanostructure embedded in the stimulus-responsive hydrogel;
    altering a property of the hydrogel by exposing the composition to a stimulus; and
    determining the change in the property of the composition, thereby determining the stimulus.

19. The method of claim 18, wherein determining the change in the property of the composition comprises detecting a change in photoluminescence.

20. The method of claim 18, wherein determining the stimulus comprises determining the presence of a chemical compound.

21. The method of claim 20, wherein the chemical compound comprises glucose.

22. The method of claim 20, wherein the chemical compound comprises glutathione.

23. The method of claim 20, wherein the chemical compound comprises an antigen.

24. The method of claim 20, wherein the chemical compound comprises NAD.

25. The method of claim 18, wherein determining the stimulus comprises determining a concentration of a chemical compound.

26. The method of claim 18, wherein determining the stimulus comprises quantifying a change in temperature of the composition.

27. The method of claim 18, wherein determining the stimulus comprises determining a pH of the composition.

28. The method of claim 18, wherein determining the stimulus comprises determining a change in a pH of the composition.

* * * * *